(12) United States Patent
Gullapalli et al.

(10) Patent No.: US 9,532,988 B2
(45) Date of Patent: Jan. 3, 2017

(54) PHARMACEUTICAL COMPOSITION COMPRISING A TRPA1 ANTAGONIST AND AN ANALGESIC AGENT

(71) Applicant: GLENMARK PHARMACEUTICALS S.A., La Chaux-de-Fonds (CH)

(72) Inventors: Srinivas Gullapalli, Navi Mumbai (IN); Praveen Kumar Gupta, Navi Mumbai (IN); Maulik Nitinkumar Gandhi, Navi Mumbai (IN)

(73) Assignee: GLENMARK PHARMACEUTICALS S.A., La Chaux-de-Fonds (CH)

( * ) Notice: Subject to any disclaimer, the term of this patent is extended or adjusted under 35 U.S.C. 154(b) by 0 days.

(21) Appl. No.: 14/513,887

(22) Filed: Oct. 14, 2014

(65) Prior Publication Data
US 2015/0105406 A1   Apr. 16, 2015

(30) Foreign Application Priority Data

Oct. 15, 2013   (IN) .................. 3247/MUM/2013

(51) Int. Cl.

| | | |
|---|---|---|
| *A01N 43/90* | (2006.01) |
| *A61K 31/519* | (2006.01) |
| *A61K 31/381* | (2006.01) |
| *A61K 31/197* | (2006.01) |
| *A61K 31/195* | (2006.01) |

(52) U.S. Cl.
CPC .......... *A61K 31/519* (2013.01); *A61K 31/195* (2013.01); *A61K 31/197* (2013.01); *A61K 31/381* (2013.01)

(58) Field of Classification Search
CPC  A61K 31/519; A61K 2300/00; A61K 31/195; A61K 31/197; A61K 31/381
See application file for complete search history.

(56) References Cited

U.S. PATENT DOCUMENTS

| | | |
|---|---|---|
| 7,465,581 B2 | 12/2008 | Bevan et al. |
| 7,951,814 B2 | 5/2011 | Muthuppalniappan et al. |
| 8,507,503 B2 | 8/2013 | Kumar et al. |
| 8,575,178 B2 | 11/2013 | Kumar et al. |
| 8,592,398 B2 | 11/2013 | Kumar et al. |
| 8,614,201 B2 | 12/2013 | Berthelot et al. |
| 2007/0196866 A1 | 8/2007 | Patapoutian et al. |
| 2009/0143377 A1 | 6/2009 | Ng et al. |
| 2009/0176883 A1 | 7/2009 | Perner et al. |
| 2011/0009430 A1 | 1/2011 | Moran et al. |
| 2012/0178766 A1 | 7/2012 | Chaudhari et al. |
| 2012/0196894 A1 | 8/2012 | Bilodeau et al. |

FOREIGN PATENT DOCUMENTS

| | | | |
|---|---|---|---|
| WO | 2008/094909 A2 | 8/2008 | |
| WO | 2009/144548 A1 | 12/2009 | |
| WO | 2009/158719 A2 | 12/2009 | |
| WO | 2010/109287 A1 | 9/2010 | |
| WO | WO 2010109334 A2 * | 9/2010 | .......... C07D 495/04 |
| WO | 2010/125469 A1 | 11/2010 | |

OTHER PUBLICATIONS

Smith et al, Vasc Health Risk Manag. Dec. 2007; 3(6): 833-844.*
Walker, et al., "The VR1 Antagonist Capsazepine Reverses Mechanical Hyperalgesia in Models of Inflammatory and Neuropathic Pain", The Journal of Pharmacology and Experimental Therapeutics, 2003, pp. 56 to 62, vol. 304—issue No. 1, The American Society for Pharmacology and Experimental Therapeutics.
Examination Report dated Sep. 23, 2016, mailed by the Australian Patent Office, in the corresponding Patent Application No. 2014335868.
Schwartz, et al., "Synergistic role of TRPV1 and TRPA1 in pancreatic pain and inflammation", Gastroenterology, 2011, pp. 1283 to 1291, vol. 140, AGA Institute.

* cited by examiner

*Primary Examiner* — Jean Cornet
(74) *Attorney, Agent, or Firm* — Pergament & Cepeda LLP; Milagros A. Cepeda; Edward D. Pergament

(57) ABSTRACT

The present patent application relates to a pharmaceutical composition comprising a TRPA1 antagonist and an analgesic agent. Particularly, the present patent application provides a pharmaceutical composition comprising a thienopyrimidinedione compound as a TRPA1 antagonist and an analgesic agent; and use of such composition for treating pain in a subject.

10 Claims, 9 Drawing Sheets

PHARMACEUTICAL COMPOSITION COMPRISING A TRPA1 ANTAGONIST AND AN ANALGESIC AGENT

PRIORITY DOCUMENT

This patent application claims priority to Indian Provisional Patent Application number 3247/MUM/2013 filed on Oct. 15, 2013, the entire contents of which are incorporated by reference herein.

TECHNICAL FIELD OF THE INVENTION

The present patent application relates to a pharmaceutical composition comprising a transient receptor potential ankyrin-1 ("TRPA1") antagonist and an analgesic agent. Particularly, the present patent application provides a pharmaceutical composition comprising a thienopyrimidinedione compound as a TRPA1 antagonist and an analgesic agent; and use of such composition for treating pain in a subject.

BACKGROUND OF THE INVENTION

Pain is described as a complex constellation of unpleasant sensory, emotional and cognitive experiences provoked by real or perceived tissue damage and is manifested by certain autonomic, psychological and behavioral reactions and is a disease of epidemic proportions. From a neurobiological perspective, pain is believed to be of three different aspects: first, pain that is an early warning physiological protective system, essential to detect and minimize contact with damaging or noxious stimuli and is called 'nociceptive pain'; second, pain that is adaptive and protective, by heightening sensory sensitivity after unavoidable tissue damage, which is mainly caused by activation of the immune system by tissue injury or infection and is normally called 'inflammatory pain'; and the third type is pain which is not protective, but maladaptive resulting from abnormal functioning of the nervous system and generally called as 'pathological pain'. This pathological pain is believed to be not a symptom of some disorder but rather a disease state of the nervous system, can occur after damage to the nervous system (neuropathic pain) or a situation where there is no such damage or inflammation (dysfunctional pain—like fibromyalgia, irritable bowel syndrome, temporomandibular joint disease, interstitial cystitis and other syndromes where there is substantial pain but no noxious stimulants and minimal/no peripheral inflammatory pathology).

Neuropathic pain is a pain caused by damage or disease that affects the somatosensory system. It may be associated with abnormal sensations called dysesthesia, and pain produced by normally non-painful stimuli (allodynia). Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain. Some treatment options for neuropathic pain include antidepressants (e.g. tricyclics and selective serotonin-norepinephrine reuptake inhibitors (SNRI's)), anticonvulsants (such as pregabalin, gabapentin, carbamazepine and oxcarbazepine and topical lidocaine. Opioid analgesics and tramadol are recognized as useful agents but are generally less recommended as first line treatments.

Analgesic agents include a group of drugs used to relieve pain and thus achieve analgesia. Analgesic drugs act in various ways on the peripheral and central nervous systems. Analgesics include various drugs such as acetaminophen (also called paracetamol), non-steroidal anti-inflammatory drugs (NSAID) that inhibit mainly the enzyme cyclooxygenase (COX) and in turn reduce the synthesis of prostaglandins, adjuvant medications that help in reduction of pain such as serotonin-norepinephrine reuptake inhibitors (SNRI), selective serotonin reuptake inhibitors (SSRI), norepinephrine reuptake inhibitors (NERIs), tricyclic antidepressants, and the likes. Examples of analgesic agents include acetaminophen, aspirin, diflunisal, ibuprofen, naproxen, fenoprofen, fenbuten, flurbiprofen, indoprofen, ketoprofen, indomethacin, ketorolac, diclofenac, nabumetone, piroxicam, meloxicam, tenoxicam, mefenamic acid, tolfenamic acid, meclofenamic acid, tolfenamic acid, celecoxib, rofecoxib, valdecoxib, parecoxib, lumiracoxib, nimesulide, licofenole, phenylbutazone, oxphenbutazone, antipyrine, aminopyrine, thiocolchicoside, duloxetine, milnacipran, amitriptylene, desipramine, imipramine, bupropion, lefetamine, methylphenidate, pregabalin, paroxetine, citalopram, clonidine, guanfacine, tizaidine morphine, oxycodone, hydromorphone, hydrocodone and the like or salts thereof.

Acetaminophen extended release tablet (TYLENOL® marketed by McNeil Cons) is indicated for management of mild to moderate pain, moderate to severe pain with adjunctive opioid analgesics and reduction of fever.

Ibuprofen is available as oral tablet (300 mg, 400 mg, 600 mg and 800 mg) and suspension (100 mg/5 mL) and used for the management of mild to moderate pain, and for management of moderate to severe pain as an adjunct to opioid analgesics.

Naproxen is available in the form of naproxen base (NAPROSYN® tablets as 250 mg, 375 mg and 500 mg; EC-NAPROSYN® delayed-release tablets as 375 mg and 500 mg and as a suspension—125 mg/5 mL), and as sodium salt (ANAPROX® tablets as 225 mg and ANAPROX DS®—500 mg) and oral suspension form (NAPROSYN®. Naproxen is indicated for the relief of the signs and symptoms of rheumatoid arthritis, osteoarthritis, ankylosing spondylitis and juvenile arthritis.

Diclofenac (VOLTAREN®-XR 100 mg extended-release tablets) is indicated for the relief of the signs and symptoms of osteoarthritis and rheumatoid arthritis.

Meloxicam (MOBIC® tablet 7.5 mg or 15 mg) and a suspension (7.5 mg/5 mL). Meloxicam is approved for the relief of the signs and symptoms of osteoarthritis, arthritis and pauciarticular or polyarticular course Juvenile Rheumatoid Arthritis in patients 2 years of age and older.

Duloxetine hydrochloride (CYMBALTA® 20 mg, 30 mg and 60 mg capsules) for the treatment of major depressive disorder (MDD), generalized anxiety disorder (GAD), for the management of neuropathic pain associated with diabetic peripheral neuropathy (DPNP), chronic musculoskeletal pain and fibromyalgia.

Pregabalin (LYRICA capsules of 25 mg, 50 mg, 75 mg, 100 mg, 150 mg, 200 mg, 225 mg, and 300 mg; and a solution of 20 mg/mL) is indicated for management of neuropathic pain associated with diabetic peripheral neuropathy (DPN), post herpetic neuralgia, fibromyalgia, and in the treatment of partial onset seizures.

Gabapentin is available as NEURONTIN capsule (100 mg, 300 mg, or 400 mg), Neurontin tablet (600 mg or 800 mg); and Neurontin oral solution (250 mg of gabapentin per 5 mL) It is indicated for management of postherpetic neuralgia and in the treatment of partial onset seizures.

Thiocolchicoside is prescribed as a skeletal muscle relaxant, anti-inflammatory, analgesic and anesthetic at doses of 2 mg, 4 mg, 8 mg and 16 mg.

It is believed TRPA1 is expressed in nociceptive neurons. Nociceptive neurons of the nervous system sense the peripheral damage and transmit pain signals. TRPA1 receptor is activated by a number of irritants that cause pain, including allyl isothiocyanate (AITC) and allicin, the pungent ingredients in mustard and garlic extracts, respectively; as well as α,β-unsaturated aldehydes, such as acrolein. The TRPA1 channel is the primary molecular site through which the pain pathway gets activated through an unusual mechanism involving covalent modification of cysteine and lysine residues within the N-terminal cytoplasmic domain of the channel protein. Thus, TRPA1 modulators are highly implicated in the alleviation of pain.

PCT Application Publication Nos. viz., WO 2004/055054, WO 2005/089206, WO 2007/073505, WO 2008/0949099, WO 2009/089082, WO 2009/002933 WO 2009/158719, WO 2009/144548, WO 2010/004390, WO 2010/109287, WO 2010/109334, WO 2010/109329, WO 2010/109328, WO 2010/125469, WO 2010/004390, WO 2011/043954 and WO 2010/141805 describe various transient receptor potential ("TRP") receptor modulators.

There still exists a need for easy to use and effective treatments for pain and further pain relieving compositions.

SUMMARY OF THE INVENTION

The present invention relates to a pharmaceutical composition comprising a TRPA1 antagonist and an analgesic agent.

A co-assigned PCT Application No. PCT/IB2010/000930 ("the '930 application", published as WO 2010/109334) discloses certain thienopyrimidinedione compounds as TRPA1 modulators.

Inter alia, the'930 application discloses TRPA1 antagonist N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (hereinafter, "Compound I") or its pharmaceutically acceptable salt. Preferably the Compound I is in the form of its potassium salt.

Another co-assigned PCT Application No. PCT/IB2011/003224 ("the '224 application", published as WO 2012/085662) also discloses certain thienopyrimidinedione compounds as TRPA1 modulators.

Inter alia, the'224 application discloses TRPA1 antagonist 4-(2,4-difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3 (2H)-yl)methyl dihydrogen phosphate (hereinafter "Compound II") or its pharmaceutically acceptable salt. Preferably the Compound II is in the form of its sodium salt.

Inter alia, the'224 application also discloses TRPA1 antagonist [4-[2,3-difluoro-4-(trifluoromethyl)phenyl]-2-{[(5,7-dimethyl-4,6-dioxo-4,5,6,7-tetrahydro[1,2]thiazolo[5,4-d]pyrimidin-3-yl)acetyl]imino}-1,3-thiazol-3(2H)-yl] methyl dihydrogen phosphate (hereinafter "Compound III") or its pharmaceutically acceptable salt.

In an embodiment, the present invention relates to a pharmaceutical composition comprising: (a) TRPA1 antagonist selected from Compound I, Compound II, Compound III and a pharmaceutically acceptable salt thereof; and (b) an analgesic agent.

The analgesic agent of the present invention includes but is not limited to acetaminophen, aspirin, diflunisal, ibuprofen, naproxen, fenoprofen, fenbuten, flurbiprofen, indoprofen, ketoprofen, indomethacin, ketorolac, diclofenac, nabumetone, piroxicam, meloxicam, tenoxicam, mefenamic acid, tolfenamic acid, meclofenamic acid, tolfenamic acid, celecoxib, rofecoxib, valdecoxib, parecoxib, lumiracoxib, nimesulide, licofenole, phenylbutazone, oxphenbutazone, antipyrine, aminopyrine, thiocolchicoside, duloxetine, milnacipran, amitriptylene, desipramine, imipramine, bupropion, lefetamine, methylphenidate, pregabalin, gabapentin, carbamazepine, oxcarbazepine venlafaxine paroxetine, citalopram, clonidine, guanfacine, tizaidine, morphine, oxycodone, hydromorphone, hydrocodone, and the like and a salt thereof. Preferably, the analgesic agent is selected from acetaminophen, aspirin, naproxen, ibuprofen, ketoprofen, indomethacin, ketorolac, diclofenac, aceclofenac, nabumetone, piroxicam, meloxicam, mefenamic acid, celecoxib, rofecoxib, nimesulide, duloxetine, thiocolchicoside, milnacipran, amitriptylene, desipramine, imipramine, bupropion, lefetamine, methylphenidate, pregabalin, gabapentin, carbamazepine, oxcarbazepine venlafaxine paroxetine, citalopram, tizaidine, morphine, oxycodone, hydromorphone, hydrocodone and a salt thereof. More preferably, the analgesic agent includes acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine venlafaxine, and a salt thereof.

In one embodiment, the pharmaceutical compositions of the invention are administered to a subject for the treatment of pain.

In the context of present invention, the pain includes but is not limited to acute pain, chronic pain, mild pain, moderate pain, severe pain, musculoskeletal pain, complex regional pain syndrome, neuropathic pain, postoperative pain, inflammatory pain, rheumatoid arthritis pain, osteoarthritis pain, back pain such as acute low back pain, visceral pain, cancer pain, neuralgia, migraine, neuropathies, acute trauma, chemotherapy—induced mononeuropathy pain states, polyneuropathy pain states (such as diabetic peripheral neuropathy & chemotherapy induced neuropathy), autonomic neuropathy pain states, peripheral nervous system (PNS) lesion or central nervous system (CNS) lesion or disease related pain states, polyradiculopathies of cervical, lumbar or sciatica type, cauda equina syndrome, piriformis syndrome, paraplegia, quadriplegia, pain states related to various Polyneuritis conditions underlying various infections, chemical injuries, radiation exposure, underlying disease or deficiency conditions (such as beriberi, vitamin deficiencies, hypothyroidism, porphyria, cancer, HIV, autoimmune disease like multiple sclerosis and spinal-cord injury, fibromyalgia, nerve injury, ischaemia, neurodegeneration, stroke, post stroke pain, inflammatory disorders, oesophagitis, gastroeosophagal reflux disorder (GERD), irritable bowel syndrome, inflammatory bowel disease, pelvic hypersensitivity, urinary incontinence, cystitis, stomach duodenal ulcer, muscle pain, pain due to colicky and referred pain.

In an embodiment, the present invention relates to a pharmaceutical composition comprising: (a) a therapeutically effective amount of TRPA1 antagonist selected from Compound I, Compound II, Compound III and a pharmaceutically acceptable salt thereof; and (b) an analgesic agent, wherein the TRPA1 antagonist and the analgesic agent are present in a weight ratio ranging from about 1:0.0001 to about 1:6000. In one aspect of this embodiment, the weight ratio of the TRPA1 antagonist to the analgesic agent ranges from about 1:0.001 to about 1:800, or from about 1:0.01 to about 1:600.

In another aspect of this embodiment, the analgesic agent is selected from a group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof. More preferably, the analgesic agent is selected from a group consisting of acetaminophen, ibuprofen, naproxen, diclofenac, meloxicam, duloxetine, thiocolchicoside, pregabalin, gabapentin and a salt thereof.

In one embodiment, pharmaceutical compositions of the present invention include TRPA1 antagonist selected from Compound I, Compound II, Compound III and a pharmaceutically acceptable salt thereof and (b) an analgesic agent, wherein the TRPA1 antagonist and the analgesic agents are present in analgesically synergistic ratio so that the analgesic activity of the combination is greater than the sum of analgesic activities of the components. Preferably, the analgesically synergistic ratio of Compound I or its salt to the analgesic agent ranges from about 1:0.01 to about 1:250, and more preferably from about 1:0.03 to about 1:20.

In one embodiment the pharmaceutical compositions of the invention are administered to a subject for the treatment of pain. In one aspect of this embodiment the pain comprises neuropathic pain, visceral pain, cancer pain, stroke pain, and inflammatory pain.

The therapeutically effective amount of TRPA1 antagonist selected from Compound I, Compound II, Compound III or a pharmaceutically acceptable salt thereof ranges from about 0.7 mg to about 1400 mg, or preferably from about 5 mg to about 1000 mg, and more preferably, from about 10 mg to about 500 mg.

In one aspect of this embodiment, the analgesic agent is selected from a group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof. More preferably, the analgesic agent is selected from a group consisting of acetaminophen, ibuprofen, naproxen, diclofenac, meloxicam, duloxetine, thiocolchicoside, pregabalin, gabapentin and a salt thereof.

In an aspect, the present invention relates to a weight ratio of TRPA1 antagonist selected from Compound I, Compound II, and a pharmaceutically acceptable salt thereof to an analgesic agent. In the context of present invention, the pharmaceutical composition comprises various weight ratios of the TRPA1 antagonist to the analgesic agent. The table below shows some of such weight ratios:

| TRPA1 antagonist | Example of analgesic agent (or its salt) | Weight ratio of the TRPA1 antagonist:the analgesic agent | Preferred Weight ratio of the TRPA1 antagonist:the analgesic agent |
|---|---|---|---|
| N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide ("Compound I") or its pharmaceutically acceptable salt | Acetaminophen | about 1:0.1 to about 1:800, or about 1:1 to about 1:400 | about 1:10 to about 1:100, or about 1:20 to about 1:50 |
| | Ibuprofen | about 1:0.01 to about 1:1000, or about 1:0.1 to about 1:400 | about 1:1 to about 1:100, or about 1:10 to about 1:50 |
| | Naproxen | about 1:0.01 to about 1:1000, or about 1:0.1 to about 1:200 | about 1:1 to about 1:100, or about 1:10 to about 1:40 |
| | Diclofenac | about 1:0.001 to about 1:500, or about 1:0.01 to about 1:100 | about 1:1 to about 1:70, or about 1:20 to about 1:50 |
| | Meloxicam | about 1:0.0001 to about 1:100 or about 1:0.005 to about 1:50 | about 1:0.01 to about 1:10, or about 1:0.05 to about 1:5. |
| | Duloxetine | about 1:0.001 to about 1:250, or about 1:0.01 to about 1:100 | about 1:1 to about 1:80, or about 1:30 to about 1:50. |
| | Thiocolchicoside | from about 1:0.005 to about 1:500, or about 1:0.001 to about 1:100 | about 1:0.05 to about 1:50, or about 1:1 to about 1:10 |
| | Pregabalin | about 1:0.001 to about 1:500, or about 1:0.01 to about 1:150 | about 1:0.1 to about 1:50, or about 1:1 to about 1:10 |
| | Gabapentin | about 1:0.001 to about 1:100, or about 1:0.01 to about 1:50 | about 1:0.05 to about 1:25, or about 1:1 to about 1:10 |
| 4-(2,4-difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3(2H)-yl)methyl dihydrogen phosphate ("Compound II") or its pharmaceutically acceptable salt | Acetaminophen | about 1:0.1 to about 1:800, or about 1:1 to about 1:400 | about 1:10 to about 1:100, or about 1:20 to about 1:50 |
| | Ibuprofen | about 1:0.01 to about 1:1000, or about 1:0.1 to about 1:400 | about 1:1 to about 1:100, or about 1:10 to about 1:50 |
| | Naproxen | about 1:0.01 to about 1:1000, or about 1:0.1 to about 1:200 | about 1:1 to about 1:100, or about 1:10 to about 1:40 |
| | Diclofenac | about 1:0.001 to about 1:500, or about 1:0.01 to about 1:100 | about 1:1 to about 1:70, or about 1:20 to about 1:50 |
| | Meloxicam | about 1:0.0001 to about 1:100 or about 1:0.005 to about 1:50 | about 1:0.01 to about 1:10, or about 1:0.05 to about 1:5. |
| | Duloxetine | about 1:0.001 to about 1:250, or about 1:0.01 to about 1:100 | about 1:1 to about 1:80, or about 1:30 to about 1:50. |
| | Thiocolchicoside | from about 1:0.005 to about 1:500, or about 1:0.001 to about 1:100 | about 1:0.05 to about 1:50, or about 1:1 to about 1:10 |
| | Pregabalin | about 1:0.001 to about 1:500, or about 1:0.01 to about 1:150 | about 1:0.1 to about 1:50, or about 1:1 to about 1:10 |
| | Gabapentin | about 1:0.001 to about 1:100, or about 1:0.01 to about 1:50 | about 1:0.05 to about 1:25, or about 1:1 to about 1:10 |
| [4-[2,3-difluoro-4-(trifluoromethyl)phenyl]-2-{[(5,7-dimethyl-4,6-dioxo-4,5,6,7-tetrahydro[1,2]thiazolo[5,4-d]pyrimidin-3-yl)acetyl] | Acetaminophen | about 1:0.1 to about 1:800, or about 1:1 to about 1:400 | about 1:10 to about 1:100, or about 1:20 to about 1:50 |
| | Ibuprofen | about 1:0.01 to about 1:1000, or about 1:0.1 to about 1:400 | about 1:1 to about 1:100, or about 1:10 to about 1:50 |
| | Naproxen | about 1:0.01 to | about 1:1 to |

-continued

| TRPA1 antagonist | Example of analgesic agent (or its salt) | Weight ratio of the TRPA1 antagonist:the analgesic agent | Preferred Weight ratio of the TRPA1 antagonist:the analgesic agent |
|---|---|---|---|
| imino}-1,3-thiazol-3(2H)-yl]methyl dihydrogen phosphate ("Compound III") or its pharmaceutically acceptable salt | Diclofenac | about 1:1000, or about 1:0.1 to about 1:200 about 1:0.001 to about 1:500, or about 1:0.01 to about 1:100 | about 1:100, or about 1:10 to about 1:40 about 1:1 to about 1:70, or about 1:20 to about 1:50 |
| | Meloxicam | about 1:0.0001 to about 1:100 or about 1:0.005 to about 1:50 | about 1:0.01 to about 1:10, or about 1:0.05 to about 1:5. |
| | Duloxetine | about 1:0.001 to about 1:250, or about 1:0.01 to about 1:100 | about 1:1 to about 1:80, or about 1:30 to about 1:50. |
| | Thiocolchicoside | about 1:0.005 to about 1:500, or about 1:0.001 to about 1:100 | about 1:0.05 to about 1:50, or about 1:1 to about 1:10 |
| | Pregabalin | about 1:0.001 to about 1:500, or about 1:0.01 to about 1:150 | about 1:0.1 to about 1:50, or about 1:1 to about 1:10 |
| | Gabapentin | about 1:0.001 to about 1:100, or about 1:0.01 to about 1:50 | about 1:0.05 to about 1:25, or about 1:1 to about 1:10 |

The weight ratio of TRPA1 antagonist selected from Compound I, Compound II, and a pharmaceutically acceptable salt thereof to acetaminophen ranges from about 1:0.01 to about 1:6000 or from about 1:0.1 to about 1:800, or from about 1:1 to about 1:400.

The weight ratio of TRPA1 antagonist selected from Compound I, Compound II, and a pharmaceutically acceptable salt thereof to naproxen ranges from about 1:0.001 to about 1:2000 or from about 1:0.01 to about 1:1000, or from about 1:0.1 to about 1:200.

The weight ratio of TRPA1 antagonist selected from Compound I, Compound II, and a pharmaceutically acceptable salt thereof to ibuprofen ranges from about 1:0.001 to about 1:5000 or from about 1:0.01 to about 1:1000, or from about 1:0.1 to about 1:400.

The weight ratio of TRPA1 antagonist selected from Compound I, Compound II, and a pharmaceutically acceptable salt thereof to diclofenac ranges from about 1:0.0001 to about 1:1000 or from about 1:0.001 to about 1:500, or from about 1:0.01 to about 1:100.

The weight ratio of TRPA1 antagonist selected from Compound I, Compound II, and a pharmaceutically acceptable salt thereof to meloxicam ranges from about 1:0.0001 to about 1:100 or from about 1:0.005 to about 1:50, or from about 1:0.01 to about 1:10.

The weight ratio of TRPA1 antagonist selected from Compound I, Compound II, and a pharmaceutically acceptable salt thereof to duloxetine ranges from about 1:0.0005 to about 1:500 or from about 1:0.001 to about 1:250, or from about 1:0.01 to about 1:100.

The weight ratio of TRPA1 antagonist selected from Compound I, Compound II, and a pharmaceutically acceptable salt thereof to pregabalin ranges from about 1:0.0001 to about 1:1000 or from about 1:0.001 to about 1:500, or from about 1:0.01 to about 1:150.

The weight ratio of TRPA1 antagonist selected from Compound I, Compound II, and a pharmaceutically acceptable salt thereof to gabapentin ranges from about 1:0.0001 to about 1:200 or from about 1:0.001 to about 1:100, or from about 1:0.01 to about 1:50.

The weight ratio of TRPA1 antagonist selected from Compound I, Compound II, and a pharmaceutically acceptable salt thereof to thiocolchicoside ranges from about 1:0.0001 to about 1:1000 or from about 1:0.005 to about 1:500, or from about 1:0.001 to about 1:100.

In one embodiment, the present invention relates to pharmaceutical composition for the treatment of pain in a subject comprising (i) a therapeutically effective amount of Compound I or its pharmaceutically acceptable salt; and (ii) an analgesic agent selected from the group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof, wherein the Compound I or its pharmaceutically acceptable salt and the analgesic agent are present in a weight ratio ranging from about 1:0.00001 to about 1:500, or from about 1:0.0001 to about 1:250, or from about 1:0.001 to about 1:100.

In one embodiment, the present invention relates to pharmaceutical composition for the treatment of neuropathic pain in a subject comprising (i) a therapeutically effective amount of Compound I or its pharmaceutically acceptable salt; and (ii) an analgesic agent selected from the group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof, wherein the Compound I or its pharmaceutically acceptable salt and the analgesic agent are present in a weight ratio ranging from about 1:0.00001 to about 1:500, or from about 1:0.0001 to about 1:250, or from about 1:0.001 to about 1:100.

In a preferred aspect of this embodiment, the analgesic agent comprises duloxetine, pregabalin, gabapentin and a salt thereof.

Neuropathic pain in context of the present invention comprises peripheral neuropathy, diabetic peripheral neuropathy (DPN), post herpetic neuralgia, spinal-cord injury pain, fibromyalgia, multiple sclerosis pain, ischemic pain, chronic musculoskeletal pain, chemotherapy-induced peripheral neuropathy, chronic inflammatory demyelinating polyneuropathy (CIDP), vasculitic neuropathy mechanical hyperalgesia, and cold allodynia.

In one embodiment, the present invention relates to a pharmaceutical composition for the treatment of neuropathic pain in a subject comprising (i) a therapeutically effective amount of Compound I or its pharmaceutically acceptable salt; and (ii) an analgesic agent selected from duloxetine, pregabalin, gabapentin and a salt thereof, wherein the weight ratio of the Compound I or its pharmaceutically acceptable salt to the analgesic agent ranges from about 1:0.001 to about 1:25.

In one aspect of this embodiment, the weight ratio of the Compound I or its pharmaceutically acceptable salt to the analgesic agent ranges from about 1:0.01 to about 1:10. In another aspect, the weight ratio of the Compound I or its pharmaceutically acceptable salt to the analgesic agent ranges from about 1:0.03 to about 1:8.

In one aspect of this embodiment, the analgesic agent is duloxetine or its salt and the weight ratio of the Compound I or its pharmaceutically acceptable salt to duloxetine or its salt ranges from about 1:0.0005 to about 1:500 or from about 1:0.001 to about 1:250 or from about 1:0.01 to about 1:50.

In another aspect of this embodiment, the analgesic agent is pregabalin or its salt and the weight ratio of the Compound I or its pharmaceutically acceptable salt to pregabalin or its salt ranges from about 1:0.0001 to about 1:1000 or from about 1:0.001 to about 1:100 or from about 1:0.01 to about 1:50.

In yet another aspect of this embodiment, the analgesic agent is gabapentin or its salt and the weight ratio of the Compound I or its pharmaceutically acceptable salt to gabapentin or its salt ranges from about 1:0.0001 to about 1:100 or from about 1:0.0025 to about 1:50 or from about 1:0.01 to about 1:10.

In one embodiment, the pharmaceutical composition of the present invention is administered by oral route in a subject in need thereof.

The pharmaceutical compositions for oral administration may be in various forms, for example, tablets, capsules, granules (synonymously, "beads" or "particles" or "pellets"), solution, suspension, emulsions, powders, dry syrups, and the like. In a preferred embodiment, the pharmaceutical composition for oral administration is in the form of a tablet or capsule.

In the context of present invention, the pharmaceutical compositions may be administered as once daily, or in divided doses two/three/four times a day. Preferably Compound I or its pharmaceutically acceptable salt may be orally administered once daily or twice daily to a subject in need thereof.

In a further embodiment, the present invention relates to a method of treating a pain in a subject, the method comprising administering the subject a pharmaceutical composition of the present invention as described herein.

In a specific embodiment, the present invention relates to a method of treating pain in a subject in need thereof comprising administering to the subject a pharmaceutical composition comprising TRPA1 antagonist selected from Compound I, Compound II, Compound III or a pharmaceutically acceptable salt thereof and an analgesic agent as described herein.

In one embodiment, the present invention relates to a method of enhancing analgesic activity of an analgesic agent comprising administering said analgesic agent in combination a TRPA1 antagonist selected from Compound I, Compound II, Compound III or a pharmaceutically acceptable salt thereof. In a preferred aspect the TRPA1 antagonist is Compound I or its pharmaceutically acceptable salt. In another preferred aspect, the analgesic agent is selected from the group consisting of naproxen, meloxicam, paracetamol, duloxetine, pregabalin, and diclofenac, gabapentin, carbamazepine, oxcarbazepine, venlafaxine, and salts thereof. In a further preferred aspect, the weight ratio of the Compound I or its pharmaceutically acceptable salt to the analgesic agent ranges from about 1:0.001 to about 1:25, or 1:0.01 to about 1:10 or preferably from about 1:0.03 to about 1:8.

In one aspect of this embodiment the Compound I, Compound II, Compound III or a pharmaceutically acceptable salt thereof and an analgesic agent are present in therapeutically effective amounts. Preferably, the compound is Compound I.

In one embodiment the present invention relates to use of TRPA1 antagonist selected from Compound I, Compound II, Compound III or a pharmaceutically acceptable salt thereof and an analgesic agent selected from the group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof in the preparation of a pharmaceutical composition of the invention for the treatment of pain in a subject. In a preferred aspect of this embodiment, pain is neuropathic pain.

DETAILED DESCRIPTION OF THE INVENTION

Figure 1:
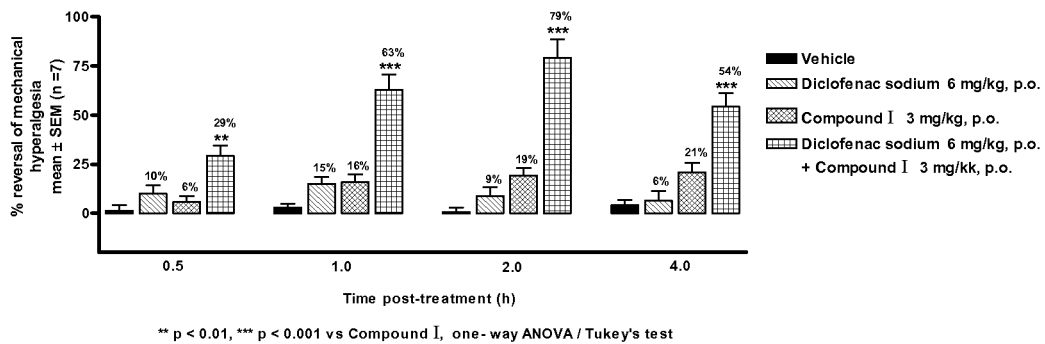
FIG. 1 is a bar graph that represents effect of Compound I (3 mg/kg), diclofenac sodium (6 mg/kg) and their combination in Freund's Complete Adjuvant (FCA)-induced mechanical hyperalgesia in male SD rats.

The present invention relates to a pharmaceutical composition comprising a TRPA1 antagonist and an analgesic agent.

A co-assigned PCT Application No. PCT/IB2010/000930 ("the '930 application", published as WO 2010/109334) discloses certain thienopyrimidinedione compounds as TRPA1 modulators.

Inter alia, the '930 application discloses TRPA1 antagonist N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (hereinafter, "Compound I") or its pharmaceutically acceptable salt. Preferably the Compound I is in the form of its potassium salt.

Another co-assigned PCT Application No. PCT/IB2011/003224 ("the '224 application", published as WO 2012/085662) also discloses certain thienopyrimidinedione compounds as TRPA1 modulators.

Inter alia, the '224 application discloses TRPA1 antagonist 4-(2,4-difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl)acetyl)imino)thiazol-3 (2H)-yl)methyl dihydrogen phosphate (hereinafter "Compound II") or its pharmaceutically acceptable salt. Preferably the Compound II is in the form of its sodium salt.

Inter alia, the '224 application also discloses TRPA1 antagonist [4-[2,3-difluoro-4-(trifluoromethyl)phenyl]-2-{[(5,7-dimethyl-4,6-dioxo-4,5,6,7-tetrahydro[1,2]thiazolo[5,4-d]pyrimidin-3-yl)acetyl]imino}-1,3-thiazol-3(2H)-yl] methyl dihydrogen phosphate (hereinafter "Compound III") or its pharmaceutically acceptable salt.

Definitions

The terms used herein are defined as follows. If a definition set forth in the present application and a definition set forth in the provisional application from which the present application claims priority are in conflict, the definition in the present application shall control the meaning of the terms.

The term "effective amount" or "therapeutically effective amount" denotes an amount of an active ingredient that, when administered to a subject for treating a respiratory disorder, produces an intended therapeutic benefit in a subject. The effective amount of TRPA1 antagonist (preferably TRPA1 antagonist selected from Compound I, Compound II, Compound III or a pharmaceutically acceptable salt thereof) as described herein ranges from about 0.7 mg to about 1400 mg, and preferably in an amount from about 5 mg to about 1000 mg, and more preferably, from about 10 mg to about 500 mg. The therapeutically effective amount of acetaminophen or its salt is present in an amount ranging from about 500 mg to about 4000 mg and preferably from about 600 mg to about 3900 mg and more preferably from about 650 mg to about 3500 mg. Preferably, the discrete dosage strengths of acetaminophen or its salt to be administered per day are 350 mg, 1000 mg, 1300 mg, 1950 mg, 2000 mg, 2600 mg, 3000 mg, 3250 mg, 3900 mg or 4000 mg. The therapeutically effective amount of naproxen or its salt is present in an amount ranging from about 200 mg to about 1000 and preferably from about 250 mg to about 900 mg and more preferably from about 375 mg to about 750 mg. Preferably, the discrete dosage strengths of naproxen or its salt to be administered per day are 250 mg or 275 mg or 375 mg or 500 mg or 550 mg or 750 mg or 1000 mg. The therapeutically effective amount of ibuprofen or its salt is present in an amount ranging from about 300 mg to about 3200 mg and preferably from about 350 mg to about 3000 mg and more preferably from about 400 mg to about 2400 mg. Preferably, the discrete dosage strengths of ibuprofen or its salt to be administered per day are 400 mg, 600 mg, 800 mg, 1200 mg, 1600 mg, 2400 mg, or 3200 mg. The therapeutically effective amount of diclofenac or its salt is present in an amount ranging from about 15 mg to about 200 mg and preferably from about 25 mg to about 150 mg and more preferably from about 25 mg to about 100 mg. Preferably, the discrete dosage strengths of diclofenac or its salt to be administered per day are 25 mg, 50 mg, 75 mg, 100 mg, 150 mg or 200 mg. The therapeutically effective amount of meloxicam or its salt is present in an amount ranging from about 1 mg to about 15 mg and preferably from about 1.5 mg to about 10 mg and more preferably from about 2 mg to about 7.5 mg. Preferably, the discrete dosage strengths of meloxicam or its salt to be administered per day are 1.5 mg, 3.0 mg, 4.5 mg, 6.0 mg, 7.5 mg, 9.0 mg, 12.5 mg or 15.0 mg.

The therapeutically effective amount of duloxetine or its salt is present in an amount ranging from about 10 mg to about 120 mg and preferably from about 15 mg to about 100 mg and more preferably from about 20 mg to about 90 mg. Preferably, the discrete dosage strengths of duloxetine or its salt to be administered per day are 20 mg, 30 mg, 40 mg, 60 mg, 90 mg or 120 mg. The therapeutically effective amount of pregabalin or its salt is present in an amount ranging from about 10 mg to about 600 mg and preferably from about 20 mg to about 400 mg and more preferably from about 25 mg to about 300 mg. Preferably, the discrete dosage strengths of pregabalin or its salt to be administered per day are 25 mg or 50 mg or 75 mg or 100 mg or 125 mg or 150 mg, or 175 mg or 200 mg or 225 mg or 250 mg or 300 mg or 400 mg or 450 mg or 500 mg or 600 mg. Therapeutically effective amount of gabapentin or its salts ranges from about 300 mg to about 3600 mg and preferably from about 600 mg to about 1800 mg and more preferably from about 900 mg to about 1200 mg. Preferably, the discrete dosage strengths of gabapentin or its salt to be administered per day are 10 mg, 20 mg, 25 mg, 50 mg, 75 mg, 100 mg, 200 mg, 300 mg, 450 mg, 600 mg, 800 mg, 1200 mg, 1800 mg, 2400 mg, 3000 mg 3600 mg. The therapeutically effective amount of thiocolchicoside or its salt is present in an amount ranging from about 1 mg to about 20 mg and preferably from about 1.5 mg to about 16 mg and more preferably from about 2 mg to about 8 mg. Preferably, the discrete dosage strengths of thiocolchicoside or its salt to be administered per day are 2 mg, 4 mg, 6 mg, 8 mg, 10 mg, 12 mg, 14 mg, or 16 mg. The therapeutically effective ranges of actives are given as above, although larger or smaller amount are not excluded if they fall within the scope of the definition of this paragraph.

The term "active ingredient" (used interchangeably with "active" or "active substance" or "drug") as used herein includes a TRPA1 antagonist, an analgesic agent or a pharmaceutically acceptable salt thereof. Preferably, the TRPA1 antagonist is N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide (hereinafter, "Compound I") or its pharmaceutically acceptable salt, or 4-(2,4-Difluoro-3-(trifluoromethyl)phenyl)-2-((2-(2,5,7-trimethyl-4,6-dioxo-4,5,6,7-tetrahydro-2H-pyrazolo[3,4-d]pyrimidin-3-yl) acetyl)imino) thiazol-3(2H)-yl)methyl dihydrogen phosphate (hereinafter, "Compound II"), or [4-[2,3-Difluoro-4-(trifluoromethyl)phenyl]-2-{[(5,7-dimethyl-4,6-dioxo-4,5,6,7-tetrahydro[1,2]thiazolo[5,4-d]pyrimidin-3-yl) acetyl]imino}-1,3-thiazol-3(2H)-yl]methyl dihydrogen phosphate (hereinafter, "Compound III"). The analgesic agent is preferably acetaminophen, aspirin, ibuprofen, naproxen, diclofenac, meloxicam, duloxetine, pregabalin, thiocolchicoside and a salt thereof.

By "salt" or "pharmaceutically acceptable salt", it is meant those salts and esters which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, propionate, acetate and lauryl sulphate salts. Representative alkali or alkaline earth metal salts include the sodium, calcium, potassium and magnesium salts.

The term "treating" or "treatment" as used herein also covers the prophylaxis, mitigation, prevention, amelioration, or suppression of a disorder modulated by the TRPA1 receptor, or the analgesic agent which acts by various mechanisms including but not limited to modulation of cyclooxygenase (COX) and lipoxygenase pathway, prostaglandin synthesis, opioid receptors, serotonin and nor-epinephrine receptors, $\alpha$-2 adrenergic receptors, or by a combination of the two in a mammal.

The "pain" includes but is not limited to acute pain, chronic pain, mild pain, moderate pain, severe pain, musculoskeletal pain, complex regional pain syndrome, neuropathic pain, postoperative pain, inflammatory pain, rheumatoid arthritis pain, osteoarthritis pain, back pain such as acute low back pain, visceral pain, cancer pain, neuralgia, migraine, neuropathies, acute trauma, chemotherapy-induced mononeuropathy pain states, polyneuropathy pain states (such as diabetic peripheral neuropathy & chemotherapy induced neuropathy), autonomic neuropathy pain states, peripheral nervous system (PNS) lesion or central nervous system (CNS) lesion or disease related pain states, polyradiculopathies of cervical, lumbar or sciatica type, cauda equina syndrome, piriformis syndrome, paraplegia, quadriplegia, pain states related to various Polyneuritis conditions underlying various infections, chemical injuries, radiation exposure, underlying disease or deficiency conditions (such as beriberi, vitamin deficiencies, hypothyroidism, porphyria, cancer, HIV, autoimmune disease like multiple sclerosis and spinal-cord injury, fibromyalgia, nerve injury, ischaemia, neurodegeneration, stroke, post stroke pain, inflammatory disorders, oesophagitis, gastroeosophagal reflux disorder (GERD), irritable bowel syndrome, inflammatory bowel disease, pelvic hypersensitivity, urinary incontinence, cystitis, stomach duodenal ulcer, muscle pain, pain due to colicky and referred pain.

The term "subject" includes mammals like human and other animals, such as domestic animals (e.g., household pets including cats and dogs) and non-domestic animals (such as wildlife). Preferably, the subject is a human.

By "pharmaceutically acceptable excipients", it is meant any of the components of a pharmaceutical composition other than the actives and which are approved by regulatory authorities or are generally regarded as safe for human or animal use.

Peripheral inflammation contributes to pain hypersensitivity through arachidonic acid based prostaglandin metabolites and their nociceptors (GPCRs) by sensitizing the primary nociceptive neurons. The transient receptor potential (TRP) based ligand-gated ion channels also known to be expressed on sensory nerves that respond to various polymodal noxious stimuli.

Oxidative stress caused by diabetes mellitus is associated with the development of chronic peripheral sensory neuropathic pain. The transient receptors potential (TRP) based ligand-gated ion channels known to be expressed on sensory nerves respond to various polymodal noxious stimuli. A known endogenous product of oxidative stress, 4-hydroxynonenal (4-HNE), was recently shown to cause pain and neurogenic inflammation through activation of TRPA1 receptor channels.

However, though the therapeutic outcomes of these two classes of drugs, the TRPA1 antagonists and the analgesic agents are similar to some extent, the mechanism of actions may vary to a good extent and thus the therapeutic effect of their combination in the treatment of pain is highly unpredictable. Particularly, the therapeutic effect of the combination of TRPA1 antagonist and an analgesic agent is highly unpredictable.

Pharmaceutical Compositions

The inventors of the present invention have surprisingly found that a pharmaceutical composition comprising a TRPA1 antagonist and an analgesic agent are more effective and show significant synergy in the treatment of pain, and provide better therapeutic value when compared to both the actives alone (when administered individually) for the treatment of pain.

In an embodiment, the present invention relates to a pharmaceutical composition comprising a TRPA1 antagonist and an analgesic agent.

In an embodiment, the present invention relates to a pharmaceutical composition comprising: (a) TRPA1 antagonist selected from Compound I, Compound II, Compound III and a pharmaceutically acceptable salt thereof; and (b) an analgesic agent.

The analgesic agent of the present invention includes but is not limited to acetaminophen, aspirin, diflunisal, ibuprofen, naproxen, fenoprofen, fenbuten, flurbiprofen, indoprofen, ketoprofen, indomethacin, ketorolac, diclofenac, nabumetone, piroxicam, meloxicam, tenoxicam, mefenamic acid, tolfenamic acid, meclofenamic acid, tolfenamic acid, celecoxib, rofecoxib, valdecoxib, parecoxib, lumiracoxib, nimesulide, licofenole, phenylbutazone, oxphenbutazone, antipyrine, aminopyrine, thiocolchicoside, duloxetine, milnacipran, amitriptylene, desipramine, imipramine, bupropion, lefetamine, methylphenidate, pregabalin, gabapentin, carbamazepine, oxcarbazepine venlafaxine paroxetine, citalopram, clonidine, guanfacine, tizaidine, morphine, oxycodone, hydromorphone, hydrocodone, and the like and a salt thereof. Preferably, the analgesic agent is selected from acetaminophen, aspirin, naproxen, ibuprofen, ketoprofen, indomethacin, ketorolac, diclofenac, aceclofenac, nabumetone, piroxicam, meloxicam, mefenamic acid, celecoxib, rofecoxib, nimesulide, duloxetine, thiocolchicoside, milnacipran, amitriptylene, desipramine, imipramine, bupropion, lefetamine, methylphenidate, pregabalin, gabapentin, carbamazepine, oxcarbazepine venlafaxine paroxetine, citalopram, tizaidine, morphine, oxycodone, hydromorphone, hydrocodone and a salt thereof. More preferably, the analgesic agent includes acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine venlafaxine, and a salt thereof.

In one embodiment the pharmaceutical compositions of the invention are administered to a subject for the treatment of pain.

In an embodiment, the present invention relates to a pharmaceutical composition comprising: (a) TRPA1 antagonist selected from Compound I, Compound II, Compound III and a pharmaceutically acceptable salt thereof; and (b) an analgesic agent, wherein the TRPA1 antagonist and the analgesic agent are present in a weight ratio ranging from about 1:0.0001 to about 1:6000. In one aspect of this embodiment the TRPA1 antagonist and the analgesic agent are present in a weight ratio ranging from about 1:0.001 to about 1:800, or from about 1:0.01 to about 1:600. In a further aspect of this embodiment the TRPA1 antagonist and the analgesic agent are present in a weight ratio ranging from about 1:0.1 to about 1:300, or from about 1:1 to about 1:50.

In one aspect of this embodiment, the analgesic agent is selected from a group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof. More preferably, the analgesic agent is selected from a group consisting of acetaminophen, ibuprofen, naproxen, diclofenac, meloxicam, duloxetine, thiocolchicoside, pregabalin, gabapentin and a salt thereof.

In one embodiment the pharmaceutical compositions of the invention are administered to a subject for the treatment of pain.

In one aspect of this embodiment the pain comprises neuropathic pain, visceral pain, cancer pain, stroke pain, and inflammatory pain.

In an embodiment, the present invention provides a pharmaceutical composition comprising therapeutically effective amount of TRPA1 antagonist selected from Compound I, Compound II, Compound III and a pharmaceutically acceptable salt thereof and an analgesic agent wherein the TRPA1 antagonist and the analgesic agent are present in a weight ratio ranging from about 1:0.0001 to about 1:6000. In one aspect of this embodiment the TRPA1 antagonist and the analgesic agent are present in a weight ratio ranging from about 1:0.001 to about 1:800, or from about 1:0.01 to about 1:600. In a further aspect of this embodiment the TRPA1 antagonist and the analgesic agent are present in a weight ratio ranging from about 1:0.1 to about 1:300, or from about 1:1 to about 1:50.

In one aspect of this embodiment, pharmaceutical compositions of the invention are administered to a subject for the treatment of pain. Preferably the pain comprises neuropathic pain, visceral pain, cancer pain, stroke pain, and inflammatory pain.

The therapeutically effective amount of TRPA1 antagonist selected from Compound I, Compound II, Compound III and a pharmaceutically acceptable salt thereof is present in an amount ranging from about 0.7 mg to about 1400 mg, and preferably from in an amount from about 5 mg to about 1000 mg, and more preferably, from about 10 mg to about 500 mg.

In one aspect of this embodiment, the analgesic agent is selected from a group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof. More preferably, the analgesic agent is selected from a group consisting of acetaminophen, ibuprofen, naproxen, diclofenac, meloxicam, duloxetine, thiocolchicoside, pregabalin, gabapentin and a salt thereof.

In one embodiment, pharmaceutical compositions of the present inception include TRPA1 antagonist selected from Compound I, Compound II, Compound III and a pharmaceutically acceptable salt thereof and (b) an analgesic agent, wherein the TRPA1 antagonist and the analgesic agents are present in analgesically synergistic ratio so that the analgesic activity of the combination is greater than the sum of analgesic activities of the components. Preferably, the analgesically synergistic ratio of Compound I or its salt and the analgesic agent ranges from about 1:0.01 to about 1:250, and more preferably from about 1:0.03 to about 1:20.

In an aspect, the present invention relates to a weight ratio of TRPA1 antagonist selected from Compound I, Compound II, or a pharmaceutically acceptable salt thereof to an analgesic agent.

The weight ratio of TRPA1 antagonist selected from Compound I, Compound II, or a pharmaceutically acceptable salt thereof to acetaminophen ranges from about 1:0.01 to about 1:6000 or from about 1:0.1 to about 1:800, or from about 1:1 to about 1:400. In a further aspect of this embodiment the weight ratio of the TRPA1 antagonist and acetaminophen ranges from about 1:10 to about 1:100, or from about 1:20 to about 1:50.

The weight ratio of TRPA1 antagonist selected from Compound I, Compound II, and a pharmaceutically acceptable salt thereof to naproxen ranges from about 1:0.001 to about 1:2000 or from about 1:0.01 to about 1:1000, or from about 1:0.1 to about 1:200. In a further aspect of this embodiment the TRPA1 antagonist and naproxen ranges from about 1:1 to about 1:100, or from about 1:10 to about 1:40.

The weight ratio of TRPA1 antagonist selected from Compound I, Compound II, and a pharmaceutically acceptable salt thereof to ibuprofen ranges from about 1:0.001 to about 1:5000 or from about 1:0.01 to about 1:1000, or from about 1:0.1 to about 1:400. In a further aspect of this embodiment the weight ratio of the TRPA1 antagonist and ibuprofen ranges from about 1:1 to about 1:100, or from about 1:10 to about 1:50.

The weight ratio of TRPA1 antagonist selected from Compound I, Compound II, and a pharmaceutically acceptable salt thereof to diclofenac ranges from about 1:0.0001 to about 1:1000 or from about 1:0.001 to about 1:500, or from about 1:0.01 to about 1:100. In a further aspect of this embodiment the weight ratio of the TRPA1 antagonist and diclofenac ranges from about 1:1 to about 1:70, or from about 1:20 to about 1:50.

The weight ratio of TRPA1 antagonist selected from Compound I, Compound II, and a pharmaceutically acceptable salt thereof to meloxicam ranges from about 1:0.0001 to about 1:100 or from about 1:0.005 to about 1:50, or from about 1:0.01 to about 1:10. In a further aspect of this embodiment the weight ratio of the TRPA1 antagonist and meloxicam ranges from about 1:0.05 to about 1:5.

The weight ratio of TRPA1 antagonist selected from Compound I, Compound II, and a pharmaceutically acceptable salt thereof to duloxetine ranges from about 1:0.0005 to about 1:500 or from about 1:0.001 to about 1:250, or from about 1:0.01 to about 1:100. In a further aspect of this embodiment the weight ratio of the TRPA1 antagonist and duloxetine ranges from about 1:1 to about 1:80, or from about 1:30 to about 1:50

The weight ratio of TRPA1 antagonist selected from Compound I, Compound II, and a pharmaceutically acceptable salt thereof to pregabalin ranges from about 1:0.0001 to about 1:1000 or from about 1:0.001 to about 1:500, or from about 1:0.01 to about 1:150. In a further aspect of this embodiment the weight ratio of the TRPA1 antagonist and pregabalin ranges from about 1:0.1 to about 1:50, or from about 1:1 to about 1:10.

The weight ratio of TRPA1 antagonist selected from Compound I, Compound II, and a pharmaceutically acceptable salt thereof to gabapentin ranges from about 1:0.0001 to about 1:200 or from about 1:0.001 to about 1:100, or from about 1:0.01 to about 1:50. In a further aspect of this embodiment the weight ratio of the TRPA1 antagonist and gabapentin ranges from about 1:0.05 to about 1:25, or from about 1:1 to about 1:10.

The weight ratio of TRPA1 antagonist selected from Compound I, Compound II, and a pharmaceutically acceptable salt thereof to thiocolchicoside ranges from about 1:0.0001 to about 1:1000 or from about 1:0.005 to about 1:500, or from about 1:0.001 to about 1:100. In a further aspect of this embodiment the weight ratio of the TRPA1 antagonist and gabapentin ranges from about 1:0.05 to about 1:50, or from about 1:1 to about 1:10.

In one embodiment, the present invention relates to pharmaceutical composition for the treatment of pain in a subject comprising (i) a therapeutically effective amount of Compound I or its pharmaceutically acceptable salt; and (ii) an analgesic agent selected from the group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof, wherein the Compound I or its pharmaceutically acceptable salt and the analgesic agent are present in a weight ratio ranging from about 1:0.00001 to about 1:500, or from about 1:0.0001 to about 1:250, or from about 1:0.001 to about 1:100.

In another aspect of this embodiment, the analgesic agent comprises acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine venlafaxine, and a salt thereof. In a preferred aspect of this embodiment, the analgesic agent comprises duloxetine, pregabalin, gabapentin and a salt thereof.

In one embodiment, the present invention relates to pharmaceutical composition for the treatment of neuropathic pain in a subject comprising (i) a therapeutically effective amount of Compound I or its pharmaceutically acceptable salt; and (ii) an analgesic agent selected from the group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof, wherein the Compound I or its pharmaceutically acceptable salt and the analgesic agent are present in a weight ratio ranging from about 1:0.00001 to about 1:500, or from about 1:0.0001 to about 1:250, or from about 1:0.001 to about 1:100.

In yet preferred aspect of this embodiment, the analgesic agent comprises duloxetine, pregabalin, gabapentin and a salt thereof.

Neuropathic pain in context of the present invention comprises peripheral neuropathy, diabetic peripheral neuropathy (DPN), post herpetic neuralgia, spinal-cord injury pain, fibromyalgia, multiple sclerosis pain, ischemic pain, chronic musculoskeletal pain, chemotherapy-induced peripheral neuropathy, chronic inflammatory demyelinating polyneuropathy (CIDP), vasculitic neuropathy mechanical hyperalgesia, and cold allodynia.

In one embodiment, the present invention relates to a pharmaceutical composition for the treatment of neuropathic pain in a subject comprising (i) a therapeutically effective amount of Compound I or its pharmaceutically acceptable salt; and (ii) an analgesic agent selected from duloxetine, pregabalin, gabapentin and a salt thereof, wherein the weight ratio of the Compound I or its pharmaceutically acceptable salt to the analgesic agent ranges from about 1:0.001 to about 1:25.

In one aspect of this embodiment, the weight ratio of the Compound I or its pharmaceutically acceptable salt to the analgesic agent ranges from about 1:0.001 to about 1:10. In another aspect, the weight ratio of the Compound I or its pharmaceutically acceptable salt to the analgesic agent ranges from about 1:0.03 to about 1:8.

In one aspect of this embodiment, the analgesic agent is duloxetine or its salt and wherein the weight ratio of the Compound I or its pharmaceutically acceptable salt to duloxetine or its salt ranges from about 1:0.0005 to about 1:500 or from about 1:0.001 to about 1:250 or from about 1:0.01 to about 1:50.

In another aspect of this embodiment, the analgesic agent is pregabalin or its salt and wherein the weight ratio of the Compound I or its pharmaceutically acceptable salt to pregabalin or its salt ranges from about 1:0.0001 to about 1:1000 or from about 1:0.001 to about 1:100 or from about 1:0.01 to about 1:50.

In yet another aspect of this embodiment, the analgesic agent is gabapentin or its salt and wherein the weight ratio of the Compound I or its pharmaceutically acceptable salt to gabapentin or its salt ranges from about 1:0.0001 to about 1:100 or from about 1:0.0025 to about 1:50 or from about 1:0.01 to about 1:10.

The pharmaceutical composition of the present invention may optionally comprise one or more pharmaceutically acceptable excipients.

In the pharmaceutical composition as described herein, the active ingredient may be in the form of a single dosage form (i.e., fixed-dose formulation in which both the active ingredients are present together) or they may be divided doses, formulated separately, each in its individual dosage forms but as part of the same therapeutic treatment, program or regimen, either once daily or two or three or four times a day.

In a further embodiment, the invention relates to a pharmaceutical composition wherein the composition is in the form of a fixed dose combination formulation of TRPA1 antagonist and the analgesic agent.

Alternately, the invention relates to a pharmaceutical composition wherein the composition is in the form of kit comprising separate formulations of TRPA1 antagonist and the analgesic agent. The separate formulations are to be administered by same or different routes, either separately, simultaneously, or sequentially, where the sequential administration is close in time or remote in time. For sequential administration, the period of time may be in the range from 10 min to 12 hours.

As contemplated herein, the active ingredients may be administered together in a single dosage form or they may be administered in different dosage forms. They may be administered at the same time or they may be administered either close in time or remotely, such as, where one drug is administered in the morning and the second drug is administered in the evening. The combination may be used prophylactically or after the onset of symptoms has occurred.

The pharmaceutical composition of the present invention may be administered orally, nasally, intra-tracheally, parenterally, transdermally, transmucosal, inhalation or by any other route that a physician or a health-care provider may determine to be appropriate. Preferably, the route of administration is oral.

In a preferred embodiment, both the active ingredients, i.e., TRPA1 antagonist and the analgesic agent are formulated as a pharmaceutical composition suitable for administration by the same route (e.g., both the actives by oral route or topical route), or by different routes (e.g., one active by oral and the other active by topical route).

In one embodiment, the pharmaceutical composition of the present invention is administered by oral route in a subject in need thereof.

The pharmaceutical compositions for oral administration may be in various forms, for example, tablets, capsules, granules (synonymously, "beads" or "particles" or "pellets"), solution, suspension, emulsions, powders, dry syrups, and the like. In a preferred embodiment, the pharmaceutical composition for oral administration is in the form of a tablet or capsule.

The capsules may contain granule/pellet/particle/mini-tablets/mini-capsules containing the active ingredients. The amount of the active agent that may be incorporated in the pharmaceutical composition may range from about 1% w/w to about 98% w/w or from about 5% w/w to about 90% w/w.

As set forth above, the pharmaceutical composition includes at least one pharmaceutically acceptable excipient, which includes but is not limited to one or more of the following; diluents, glidants and lubricants, preservatives, buffering agents, chelating agents, polymers, gelling agents/viscosifying agents, surfactants, solvents and the like.

In the context of present invention, the pharmaceutical compositions may be administered as once daily, or in divided doses two/three/four times a day. Preferably Compound I or its pharmaceutically acceptable salt may be orally administered once daily or twice daily to a subject in need thereof.

In a further embodiment, the present invention relates to a method of treating a pain in a subject, the method comprising administering the subject a pharmaceutical composition of the present invention.

In a specific embodiment, the present invention relates to a method of treating pain in a subject in need thereof comprising administering to the subject a pharmaceutical composition comprising TRPA1 antagonist selected from Compound I, Compound II, Compound III or a pharmaceutically acceptable salt thereof and an analgesic agent.

In one embodiment, the present invention relates to a method of enhancing analgesic activity of an analgesic agent comprising administering said analgesic agent in combination a TRPA1 antagonist selected from Compound I, Compound II, Compound III or a pharmaceutically acceptable salt thereof. In a preferred aspect the TRPA1 antagonist is Compound I or its pharmaceutically acceptable salt. In another preferred aspect, the analgesic agent is selected from the group consisting of naproxen, meloxicam, paracetamol, duloxetine, pregabalin, and diclofenac, gabapentin, carbamazepine, oxcarbazepine, venlafaxine, and salts thereof. In a further preferred aspect, the weight ratio of the Compound I or its pharmaceutically acceptable salt to the analgesic agent ranges from about 1:0.001 to about 1:25, or 1:0.01 to about 1:10 or preferably from about 1:0.03 to about 1:8.

In one aspect of this embodiment the Compound I, Compound II, Compound III or a pharmaceutically acceptable salt thereof and an analgesic agent are present in therapeutically effective amounts. Preferably, the compound is Compound I.

In another aspect of this embodiment the pain is neuropathic pain. In a further aspect, the neuropathic pain comprises peripheral neuropathy, diabetic peripheral neuropathy (DPN), post herpetic neuralgia, spinal-cord injury pain, fibromyalgia, multiple sclerosis pain, ischemic pain, chronic musculoskeletal pain, chemotherapy-induced peripheral neuropathy, chronic inflammatory demyelinating polyneuropathy (CIDP), vasculitic neuropathy mechanical hyperalgesia, and cold allodynia.

In one embodiment the present invention relates to use of TRPA1 antagonist selected from Compound I, Compound II, Compound III or a pharmaceutically acceptable salt thereof and an analgesic agent selected from the group consisting of acetaminophen, aspirin, ibuprofen, naproxen, diclofenac, meloxicam, duloxetine, thiocolchicoside, milnacipran, amitriptylene, desipramine, pregabalin, gabapentin, carbamazepine, oxcarbazepine, venlafaxine, thiocolchicoside, and a salt thereof in the preparation of a pharmaceutical composition of the invention for the treatment of pain in a subject. In a preferred aspect of this embodiment the pain is neuropathic pain. In a further aspect, the neuropathic pain comprises peripheral neuropathy, diabetic peripheral neuropathy (DPN), post herpetic neuralgia, spinal-cord injury pain, fibromyalgia, multiple sclerosis pain, ischemic pain, chronic musculoskeletal pain, chemotherapy-induced peripheral neuropathy, chronic inflammatory demyelinating polyneuropathy (CIDP), vasculitic neuropathy mechanical hyperalgesia, and cold allodynia.

Various animal models can be used for the evaluation of the therapeutic efficacy of drug candidates for pain-related disorders such as inflammatory disorders, nerve injury, and central injury models of pain. Each model mirrors the clinical appearance of many features of the pain disorder, and human conditions such as rheumatoid arthritis and osteoarthritis related pain states, diabetic neuropathy, nerve injury models of mononeuropathies, chemotherapy and immunotherapy related pain states. All these models have allowed for the comparison of certain behavioral, cellular, biochemical, and molecular mechanisms with human patient populations.

Models to best describe acute pain are acute tests, such as hot-plate, tail-flick, and paw pressure tests. There are few models used for tonic pain that use long-duration stimuli tests. These tests use heat/infrared irradiation, noxious pressure or pinch under the presence of various irritants, or foreign chemical agent as nociceptive stimulus which are usually administered intradermally or intraperitoneally. The response to irritant or foreign chemical agent is thus computed into score that acts as a result marker for the test.

Chronic inflammatory pain models use the intracapsular administration of urate crystals, Freund's adjuvant, capsaicin, or carrageenan. Such long-term tonic pain in rats has been used to model human arthritis and to examine the safety and efficacy of various NSAIDs including the COX-1 and COX-2 inhibitors commonly used by patients for inflammatory pain. Formalin (37% solution of formaldehyde) is the most commonly used agent for intraperitoneal/intradermal paw injections. Other agents used are hypertonic saline, Freund's adjuvant, ethylene diamine tetra-acetic acid (EDTA), or capsaicin. Intraperitoneal injection of agents provokes a stereotypical behavior in rodents that is characterized by abdominal contractions, whole body movements, contortions of the abdominal muscles, and reduced motor activity and in coordination. In this test, commonly called the "writhing test," the behaviors are considered reflexive, and are evidence of peritoneovisceral or visceral pain associated with visceral chemoreceptors.

In an embodiment, the present invention provides a process for the preparing a pharmaceutical composition comprising TRPA1 antagonist selected from Compound I, Compound II, Compound III or a pharmaceutically acceptable salt thereof an analgesic agent and a pharmaceutically acceptable excipient, wherein the composition is in the form of a fixed dose combination formulation. The process comprises admixing TRPA1 antagonist selected from Compound I, Compound II, Compound III or a pharmaceutically acceptable salt thereof with the analgesic agent. Alternately, the process comprises formulating TRPA1 antagonist selected from Compound I, Compound II, Compound III or a pharmaceutically acceptable salt thereof and the analgesic agent in such a way that they are not in intimate contact with each other. The analgesic agent is preferably selected from acetaminophen, aspirin, ibuprofen, naproxen, diclofenac, meloxicam, duloxetine, pregabalin, gabapentin, thiocolchicoside, carbamazepine, oxcarbazepine venlafaxine and a salt thereof.

The process for making the pharmaceutical composition may, for example include, (1) granulating either or both the active ingredients, combined or separately, along with pharmaceutically acceptable carriers so as to obtain granulate, and (2) converting the granulate into suitable dosage forms for oral administration. The typical processes involved in preparation of pharmaceutical combinations include various unit operations such as mixing, sifting, solubilizing, dispersing, granulating, lubricating, compressing, coating, and the like. These processes, as contemplated by a person skilled in the art, have been incorporated herein for preparing the pharmaceutical composition.

It will be understood that various modifications may be made to the embodiments disclosed herein. Therefore the above description should not be construed as limiting, but merely as exemplifications of preferred embodiments. Other arrangements and methods may be implemented by those skilled in the art without departing from the scope and spirit of this invention.

All publications, patents, and patent applications cited in this application are herein incorporated by reference to the same extent as if each individual publication, patent, or patent application was specifically and individually indicated to be incorporated herein by reference.

The following examples are provided to enable one skilled in the art to practice the invention and are merely illustrative of the invention. The examples should not be read as limiting the scope of the invention.

EXAMPLES

Example 1

The Effect of Compound I, Diclofenac Sodium and their Combination in Freund's Complete Adjuvant (FCA)-Induced Inflammatory Mechanical Hyperalgesia in Male SD Rats Materials: FCA containing 1 mg/ml of heat killed and dried *Mycobacterium tuberculosis* (H37RA strain) emulsified in mineral oil and mannide mono-oleate; Male SD rats weighing 170-220 g; Paw Pressure Analgesymeter (37215, Ugo Basile, Comerio, Italy); Compound I potassium; and Diclofenac sodium The in vivo screening of Compound I potassium and diclofenac sodium based combinational efficacy in FCA-induced model of inflammatory pain/hyperalgesia in rats was done according to the modified procedure described in Walker K M et al., *JPET* 2003, 304:56-62. The screening of the compounds can also be carried out by some other methods, procedures or models known to persons skilled in the art.

Naïve withdrawal thresholds of the left hind paw to an increasing pressure (g) stimulus were measured in rats using the analgesymeter. FCA was injected (30 μl) into the plantar region of left paw of rats to induce the inflammatory hyperalgesia. Mechanical hyperalgesia (24 h after FCA injection) was assessed by measuring hind paw withdrawal thresholds. Animals were grouped according to Table 1.

Rats were orally dosed with vehicle, diclofenac sodium, Compound I potassium and combination (diclofenac sodium+Compound I potassium). The effect of Compound I potassium, diclofenac sodium and their combination, in FCA-induced inflammatory mechanical hyperalgesia in male SD rats, was evaluated using Randall-Sellitto paw pressure analgesymeter (37215, Ugo Basile, Comerio, Italy) fitted with a wedge-shaped probe. The post-dose paw withdrawal thresholds were measured at 0.5, 1, 2 & 4 h after oral administration. The percentage (%) reversal of mechanical hyperalgesia was calculated as per standard procedure.

Compound I (3 mg/kg) and diclofenac sodium (6 mg/kg) produced only moderate effect with a maximal of 21 & 15% reversal of hyperalgesia during the entire course of the study, respectively. However, the combination of Compound I and diclofenac sodium produced surprisingly superior efficacy compared to the sum of efficacies of individual agents as shown in FIG. 1. The combination produced a maximum of 79% reversal of hyperalgesia in the study.

TABLE 1

| | | Dose (mg/kg) | | | |
|---|---|---|---|---|---|
| Group | Treatment | Diclofenac sodium | Compound I | Route | No. of animals (N) |
| 1 | Vehicle | — | — | p.o. | 7 |
| 2 | Diclofenac sodium | 6 | — | p.o. | 7 |
| 3 | Compound I | — | 3 | p.o. | 7 |
| 4 | Combination | 6 | 3 | p.o. | 7 |

In a separate experiment, this combination study was also done at different doses of both drugs as described below. Animals were grouped according to Table 2.

TABLE 2

| | | Dose (mg/kg) | | | |
|---|---|---|---|---|---|
| Group | Treatment | Diclofenac sodium | Compound I | Route | No. of animals (N) |
| 1 | Vehicle | — | — | p.o. | 7 |
| 2 | Diclofenac sodium | 8 | — | p.o. | 7 |
| 3 | Compound I | — | 1 | p.o. | 7 |
| 4 | Combination | 8 | 1 | p.o. | 7 |

Figure 2:
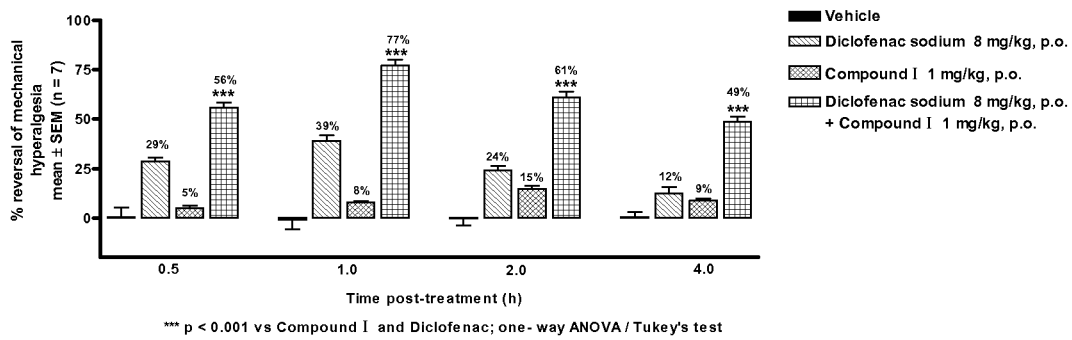
FIG. 2 is a bar graph that represents effect of Compound I (1 mg/kg), diclofenac sodium (8 mg/kg) and their combination in Freund's Complete Adjuvant (FCA)-induced mechanical hyperalgesia in male SD rats.

Compound I (1 mg/kg) and diclofenac sodium (8 mg/kg) produced only moderate effect with a maximal of 15 & 39% reversal of hyperalgesia, respectively. However, the combination of Compound I and diclofenac sodium produced significantly superior efficacy (synergistic effect) compared to the sum of efficacies of individual agents as shown in FIG. 2. The combination has produced a maximum of 77% reversal of hyperalgesia.

Example 2

Effect of Compound I, Naproxen and their Combination in FCA-Induced Inflammatory Mechanical Hyperalgesia in SD Rats The animal study was carried out according to the method described in Example 1. The male SD rats were grouped according to Table 3.

TABLE 3

| | | Dose (mg/kg) | | | |
|---|---|---|---|---|---|
| Group | Treatment | Naproxen | Compound I | Route | No. of animals (N) |
| 1 | Vehicle | — | — | p.o. | 7 |
| 2 | Naproxen | 3 | — | p.o. | 7 |
| 3 | Compound I | — | 3 | p.o. | 7 |
| 4 | Combination | 3 | 3 | p.o. | 7 |

Figure 3:
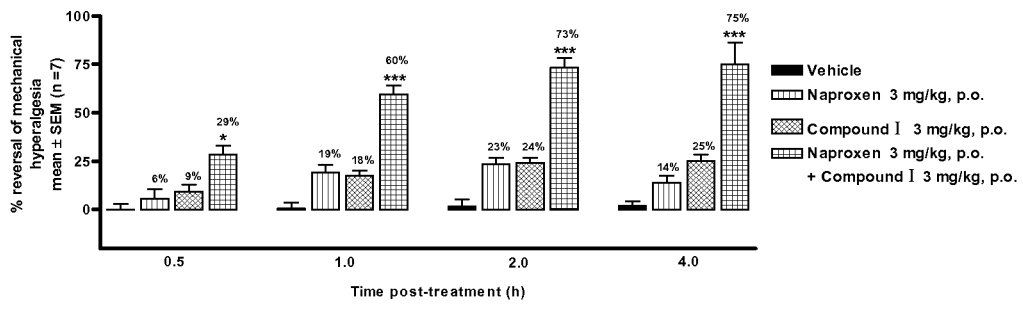
FIG. 3 is a bar graph that represents effect of Compound I (3 mg/kg), naproxen (3 mg/kg) and their combination in Freund's Complete Adjuvant (FCA)-induced mechanical hyperalgesia in male SD rats.

Compound I (3 mg/kg) and naproxen (3 mg/kg) produced only moderate effect with a maximal of 25 & 23% reversal of hyperalgesia, respectively. However, the combination of Compound I and naproxen produced significantly synergistic efficacy (a maximum of 75% reversal of hyperalgesia) across the course of study compared to the sum of efficacies of individual agents as shown in FIG. 3.

In a separate experiment, the study was also done for following groups as in Table 4.

TABLE 4

| | | Dose (mg/kg) | | | |
|---|---|---|---|---|---|
| Group | Treatment | Naproxen | Compound I | Route | No. of animals (N) |
| 1 | Vehicle | — | — | p.o. | 6 |
| 2 | Naproxen | 5 | — | p.o. | 7 |
| 3 | Compound I | — | 1 | p.o. | 7 |
| 4 | Combination | 5 | 1 | p.o. | 7 |

Figure 4:
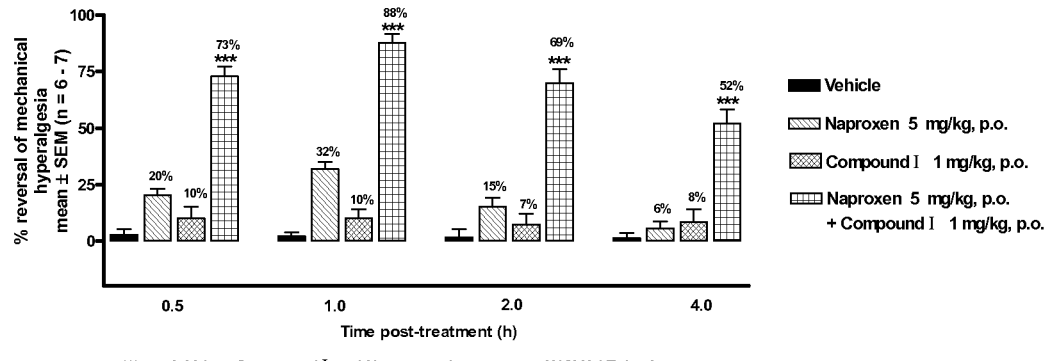
FIG. 4 is a bar graph that represents effect of Compound I (1 mg/kg), naproxen (5 mg/kg) and their combination in Freund's Complete Adjuvant (FCA)-induced mechanical hyperalgesia in male SD rats.

Compound I (1 mg/kg) and Naproxen (5 mg/kg) produced only moderate effect with a maximal of 10 & 32% reversal of hyperalgesia, respectively. Combination of Compound I and Naproxen produced significantly superior efficacy (synergistic effect) across the course of study compared to the sum of efficacies of individual agents as shown in FIG. 4. The combination has produced a maximum of 88% reversal of hyperalgesia.

Example 3

Effect of Compound I, Naproxen and their Combination in Monosodium Iodo Acetate (MIA)-Osteoarthritis Model of Inflammatory Model of Healthy Male Sprague-Dawley (SD) Rats After recording basal weight borne by both hind limbs (naïve) using the incapacitance meter (IITC Inc), rats were briefly anaesthetized with 2% isoflurane and $O_2$ mixture and given intraarticular (i.a.) injection of MIA (5 mg per rat in 50 nl) through the intrapatellar ligament of the left knee (Combe et al., 2004). MIA was dissolved in 0.9% sterile saline and administered using a 26½ gauge needle. Contralateral knees were injected intra-articularly with 50 µl of 0.9% sterile saline. Weight bearing deficit in ipsilateral paw was assessed 20 h post MIA injection by measuring weight borne by both hind limbs.

On the day of the experiment (20 h after MIA injection), rats were evaluated for pre-dose weight bearing deficit to assess the effect of MIA. After regrouping the rats after randomization, the pre- & post-dose weight bearing deficit, was assessed for both hind limbs. Rats were orally dosed with vehicle, naproxen, compound I potassium salt and combination (Naproxen+Compound I—simultaneously). The effect of compound I, naproxen and their combination, in MIA-osteoarthritis induced weight bearing deficit in male SD rats, was evaluated using Incapacitance meter (IITC Inc.) fitted with a perspex chamber designed so that each hind paw rat rests on separate transducer pads to record animal's weight on each paw. The post-dose weight bearing were measured at 0.5, 1, 2 & 4 h after oral administration. The % reversal of weight bearing deficit was calculated as per standard procedure. The male SD rats were grouped according to Table 5.

TABLE 5

| Group | Treatment | Dose (mg/kg) Naproxen | Compound I | Route | No. of animals (N) |
|---|---|---|---|---|---|
| 1 | Vehicle | — | — | p.o. | 8 |
| 2 | Naproxen | 10 | — | p.o. | 8 |
| 3 | Compound I | — | 1 | p.o. | 8 |
| 4 | Combination | 10 | 1 | p.o. | 8 |

Figure 5:
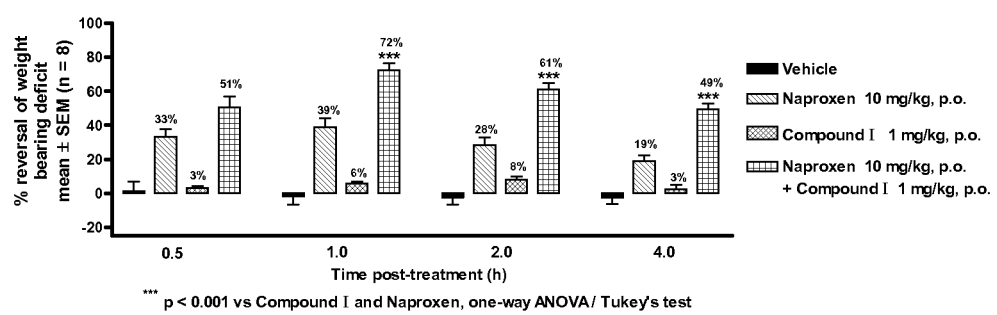
FIG. 5 is a bar graph that represents effect of Compound I (1 mg/kg), naproxen (10 mg/kg) and their combination in Monosodium Iodo Acetate (MIA)-osteoarthritis model of inflammatory model of healthy male Sprague-Dawley (SD) rats.

Compound I (1 mg/kg) and naproxen (10 mg/kg) produced only moderate effect with a maximal of 8 & 39% reversal of weight bearing deficit respectively. Combination of Compound I and naproxen produced significantly superior efficacy (synergistic effect) compared to the sum of efficacies of individual agents as shown in FIG. 5. The combination has produced a maximum of 72% reversal of weight bearing deficit.

Example 4

The Effect of Compound I, Meloxicam and their Combination in FCA-Induced Inflammatory Mechanical Hyperalgesia in Male SD Rats The animal study was carried out according to the method described in Example 1. The male SD rats were grouped according to Table 6.

TABLE 6

| Group | Treatment | Dose (mg/kg) Meloxicam | Compound I | Route | No. of animals (N) |
|---|---|---|---|---|---|
| 1 | Vehicle | — | — | p.o. | 7 |
| 2 | Meloxicam | 0.5 | — | p.o. | 7 |
| 3 | Compound I | — | 3 | p.o. | 7 |
| 4 | Combination | 0.5 | 3 | p.o. | 7 |

Figure 6:
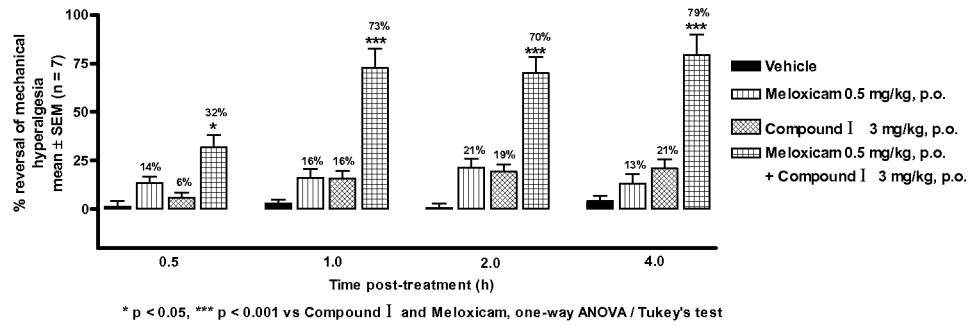
FIG. 6 is a bar graph that represents effect of Compound I (3 mg/kg), meloxicam (0.5 mg/kg) and their combination in Monosodium Iodo Acetate (MIA)-osteoarthritis model of inflammatory model of healthy male Sprague-Dawley (SD) rats

Compound I (3 mg/kg) and meloxicam (0.5 mg/kg) produced only moderate effect with a maximal of 21 & 21% reversal of hyperalgesia respectively. It was surprisingly found that combination of Compound I and meloxicam produced significantly superior efficacy (synergistic effect) compared to the sum of efficacies of individual agents as shown in FIG. 6. The combination produced a maximum of 79% reversal of hyperalgesia.

Example 5

The Effect of Compound I, Paracetamol and their Combination in FCA-Induced Inflammatory Mechanical Hyperalgesia in Male SD Rats The animal study was carried out according to the method described in Example 1. The male SD rats were grouped according to Table 7.

TABLE 7

| Group | Treatment | Dose (mg/kg) Paracetamol | Compound I | Route | No. of animals (N) |
|---|---|---|---|---|---|
| 1 | Vehicle | — | — | p.o. | 7 |
| 2 | Paracetamol | 60 | — | p.o. | 7 |
| 3 | Compound I | — | 3 | p.o. | 7 |
| 4 | Combination | 60 | 3 | p.o. | 7 |

Figure 7:
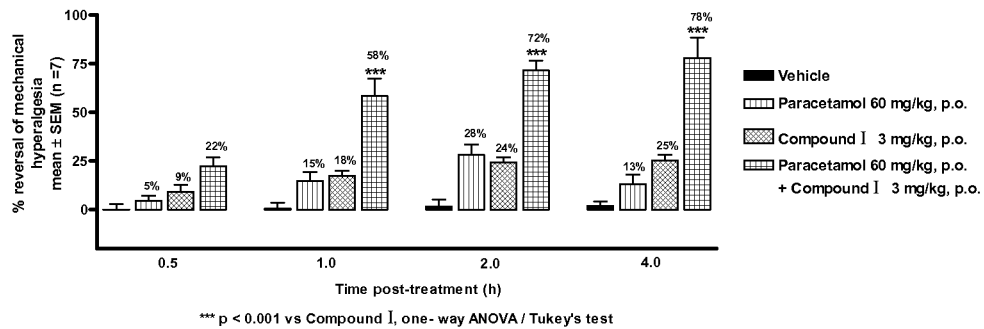
FIG. 7 is a bar graph that represents effect of Compound I (3 mg/kg), paracetamol (60 mg/kg) and their combination in Monosodium Iodo Acetate (MIA)-osteoarthritis model of inflammatory model of healthy male Sprague-Dawley (SD) rats.

Compound I (3 mg/kg) and paracetamol (60 mg/kg) produced only moderate effect with a maximal of 25 & 28% reversal of hyperalgesia respectively. Combination of Compound I and paracetamol produced superior synergistic efficacy (with a maximum of 78% reversal of hyperalgesia) compared to the sum of efficacies of individual agents as shown in FIG. 7.

Example 6

The Effect of Combinational of Compound I and Thiocolchicoside in FCA Model of Inflammatory Pain in Healthy Male SD Rats The animal study was carried out according to the method described in Example 1. The male SD rats were grouped according to Table 8.

TABLE 8

| Group | Treatment | Dose (mg/kg) Thiocolchicoside | Compound I | Route | No. of animals (N) |
|---|---|---|---|---|---|
| 1 | Vehicle | — | — | p.o. | 7 |
| 2 | Thiocolchicoside | 0.01 | — | p.o. | 7 |
| 3 | Compound I | — | 3 | p.o. | 7 |
| 4 | Combination | 0.01 | 3 | p.o. | 7 |

Figure 8:
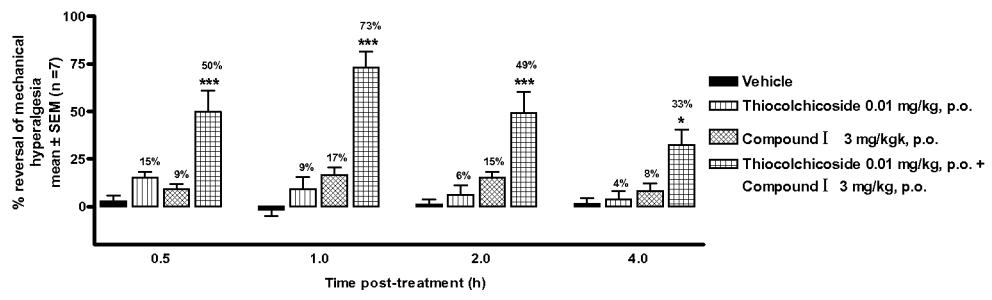
FIG. 8 is a bar graph that represents effect of Compound I (3 mg/kg), thiocolchicoside (0.01 mg/kg) and their combination in Monosodium Iodo Acetate (MIA)-osteoarthritis model of inflammatory model of healthy male Sprague-Dawley (SD) rats.
Figure 9:
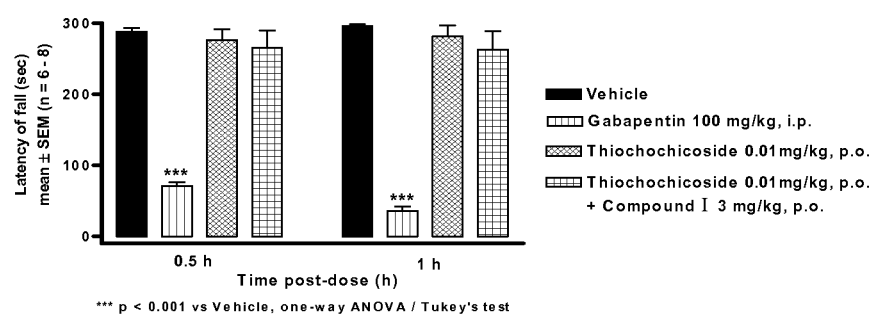
FIG. 9 is a bar graph that represents effect of Compound I (3 mg/kg), thiocolchicoside (0.01 mg/kg) and their combination on motor coordination in rotarod test in male SD rats.

Compound I (3 mg/kg) and thiocolchicoside (0.01 mg/kg) produced only moderate effect with a maximal of 17 & 15% reversal of hyperalgesia respectively. However, the combination of Compound I and thiocolchicoside produced significantly superior efficacy (synergistic effect) compared to the sum of efficacies of individual agents as shown in FIG. 8. The combination produced a maximum of 73% reversal of hyperalgesia. In addition, chosen dose of thiocolchicoside alone and in combination with Compound I did not produce any motor deficits as shown in FIG. 9.

Example 7

To Study the Combinational Effect of Compound I and Duloxetine Hydrochloride (HCl) in Streptozotocin-Induced Diabetic Peripheral Neuropathic Hyperalgesia in Male Sprague-Dawley (SD) Rats Streptozotocin (STZ)-induced neuropathic hyperalgesia in rats is a model to screen potential therapeutics for diabetic painful neuropathy in human patients. Streptozotocin was dissolved in freshly prepared cold citrate buffer (0.1 M, pH—4.4). Diabetes was induced in overnight fasted male SD rats (weighing 250-300 g) by a single intraperitoneal injection of Streptozotocin (Sigma, 55 mg/kg, i.p). Blood glucose was assayed 1 week post STZ injection using blood glucose meter (Contor TS, Bayer Health Care, India) and animals exhibiting >260 mg/dl blood glucose were considered diabetic and inducted into the study. On the day of the experiment (13$^{th}$ day after STZ injection) rats were assessed for mechanical hyperalgesia using Randall-Sellito paw pressure analgesymeter. Animals were weighed and grouped as described in Table 9.

Mechanical hyperalgesia was assessed both pre- and post-dosing of drugs by measuring hind paw withdrawal thresholds. Rats were orally dosed with vehicle, duloxetine hydrochloride, Compound I potassium salt and combination (Duloxetine+Compound I). The post-dose paw withdrawal thresholds were measured at 0.5, 1, 2 & 4 h after oral administration. The % reversal of mechanical hyperalgesia was calculated as per standard procedure.

TABLE 9

| | | Dose (mg/kg) | | No. of animals |
|---|---|---|---|---|
| Group | Treatment | Duloxetine HCl | Compound I | Route | (N) |
| 1 | Vehicle | — | — | p.o. | 7 |
| 2 | Duloxetine HCl | 3 | — | p.o. | 7 |
| 3 | Compound I | — | 3 | p.o. | 7 |
| 4 | Combination | 3 | 3 | p.o. | 7 |

Figure 10:
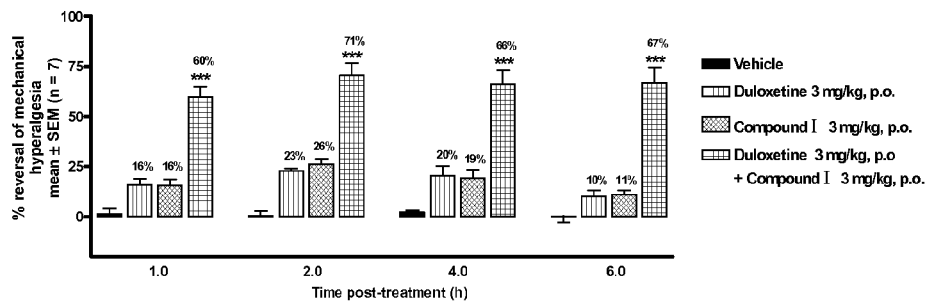
FIG. 10 is a bar graph that represents effect of Compound I (3 mg/kg) and Duloxetine hydrochloride (HCl) (3 mg/kg) in streptozotocin-induced diabetic peripheral neuropathic hyperalgesia in male Sprague-Dawley (SD) rats.

Compound I (3 mg/kg) and duloxetine hydrochloride (3 mg/kg) produced only moderate effect with a maximal of 26 & 23% reversal of hyperalgesia during the course of the study, respectively. However, combination of Compound I and duloxetine hydrochloride surprisingly produced a synergistic effect (a maximum of 71% reversal of hyperalgesia) compared to the sum of efficacies of individual agents as shown in FIG. 10.

In a separate set of experiment, animals were weighed and grouped as described in Table 10.

TABLE 10

| | | Dose (mg/kg) | | | No. of animals |
|---|---|---|---|---|---|
| Group | Treatment | Duloxetine HCl | Compound I | Route | (N) |
| 1 | Vehicle | — | — | p.o. | 8 |
| 2 | Duloxetine HCl | 10 | — | p.o. | 8 |
| 3 | Compound I | — | 1 | p.o. | 8 |
| 4 | Combination | 10 | 1 | p.o. | 8 |

Figure 11:
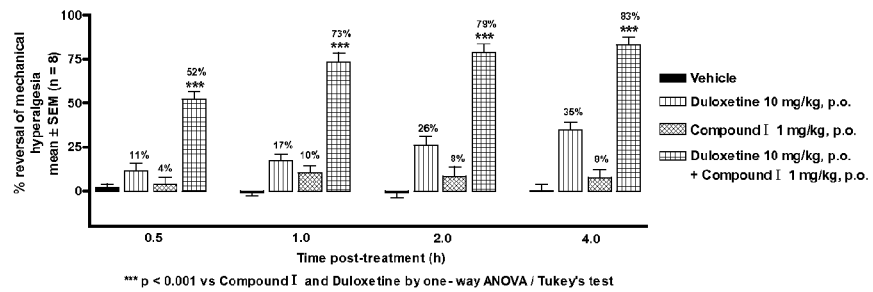
FIG. 11 is a bar graph that represents effect of Compound I (1 mg/kg) and Duloxetine hydrochloride (HCl) (10 mg/kg) in streptozotocin-induced diabetic peripheral neuropathic hyperalgesia in male Sprague-Dawley (SD) rats.

Compound I (1 mg/kg) and duloxetine hydrochloride (10 mg/kg) produced only moderate effect with a maximal of 10 & 35% reversal of hyperalgesia respectively. Combination of Compound I and duloxetine hydrochloride produced significantly superior efficacy (synergistic effect) compared to the sum of efficacies of individual agents as shown in FIG. 11. The combination has produced a maximum of 83% reversal of hyperalgesia.

Example 8

Combinational Efficacy Study of Compound I Potassium Salt and Pregabalin in Chronic Constriction Injury (CCI)-Induced Neuropathic Pain The objective of this experiment was to study the combinational effect of Compound I and pregabalin in CCI-induced neuropathic hyperalgesia in male SD rats. Male SD rats weighing 180-220 g were grouped according to Table 11. Rats were anesthetized using ketamine/xylazine (40/5 mg/kg, i.p.) and the left sciatic nerve was exposed at mid-thigh level through a small incision. Four loose ligatures of 4-0 chromic cat gut at 1 mm space were placed around the sciatic nerve after the bifurcation of common sciatic nerve. After 6-7 days, mechanical hyperalgesia was assessed by measuring hind paw withdrawal thresholds to an increasing pressure (g) stimulus, using the Randall-Sellitto analgesymeter (Ugo Basile, Italy), fitted with a wedge-shaped probe.

Mechanical hyperalgesia was assessed both pre- and post-dosing of drugs by measuring hind paw withdrawal thresholds. Rats were orally dosed with vehicle, pregabalin, Compound I potassium salt and combination (Pregabalin+Compound I). The post-dose paw withdrawal thresholds were measured at 0.5, 1, 2 & 4 h after oral administration. The % reversal of mechanical hyperalgesia was calculated as per standard procedure.

TABLE 11

| | | Dose (mg/kg) | | | No. of |
|---|---|---|---|---|---|
| Group | Treatment | Pregabalin | Compound I | Route | animals (N) |
| 1 | Vehicle | — | — | p.o. | 7 |
| 2 | Pregabalin | 1 | — | p.o. | 7 |
| 3 | Compound I | — | 3 | p.o. | 7 |
| 4 | Combination | 1 | 3 | p.o. | 7 |

Figure 12:
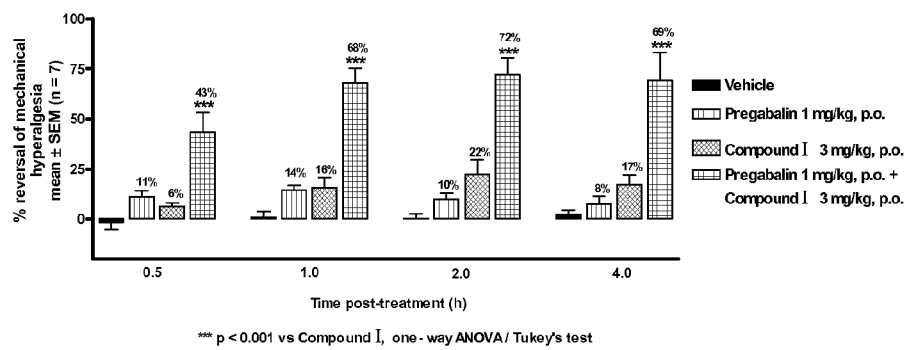
FIG. 12 is a bar graph that represents effect of Compound I potassium salt (3 mg/kg), pregabalin (1 mg/kg) and their combination in chronic constriction injury (CCI)-induced mechanical hyperalgesia in diabetic male SD rats.

Compound I (3 mg/kg) and pregabalin (1 mg/kg) produced only moderate effect, with a maximal of 22 & 14% reversal of hyperalgesia, respectively. Surprisingly, a combination of Compound I and pregabalin produced significantly superior efficacy compared to the sum of efficacies of individual agents as shown in FIG. 12. The combination produced a maximum of 72% reversal of hyperalgesia.

Example 9

The Effect of Compound II Disodium Salt and Diclofenac Sodium, and their Combination in FCA-Induced Inflammatory Mechanical Hyperalgesia in Male SD Rats Naïve withdrawal thresholds of the left hind paw to an increasing pressure (g) stimulus were measured in rats using the analgesymeter. Freund's Complete Adjuvant (FCA) was injected (30 µl) into the plantar region of left paw of rats to induce the inflammatory hyperalgesia. Mechanical hyperalgesia (24 h after FCA injection) was assessed both pre- & post-dosing of drugs by measuring hind paw withdrawal thresholds. Rats were orally dosed with vehicle, Diclofenac sodium, Compound II disodium salt and combination (Diclofenac sodium+Compound II—simultaneously). The effect of Compound II, Diclofenac sodium and their combination, in FCA-induced inflammatory mechanical hyperalgesia in male SD rats, was evaluated using Randall-Sellitto paw pressure analgesymeter (37215, Ugo Basile, Comerio, Italy) fitted with a wedge-shaped probe. The post-dose paw withdrawal thresholds were measured at 0.5, 1, 2 & 4 h after oral administration. The % reversal of mechanical hyperalgesia was calculated. Animals were weighed and grouped as described in Table 12.

TABLE 12

| Group | Treatment | Dose (mg/kg) Diclofenac sodium | Dose (mg/kg) Compound II | Route | No. of animals (N) |
|---|---|---|---|---|---|
| 1 | Vehicle | — | — | p.o. | 6 |
| 2 | Diclofenac sodium | 6 | — | p.o. | 6 |
| 3 | Compound II | — | 0.13 | p.o. | 7 |
| 4 | Combination | 6 | 0.13 | p.o. | 7 |

Figure 13:
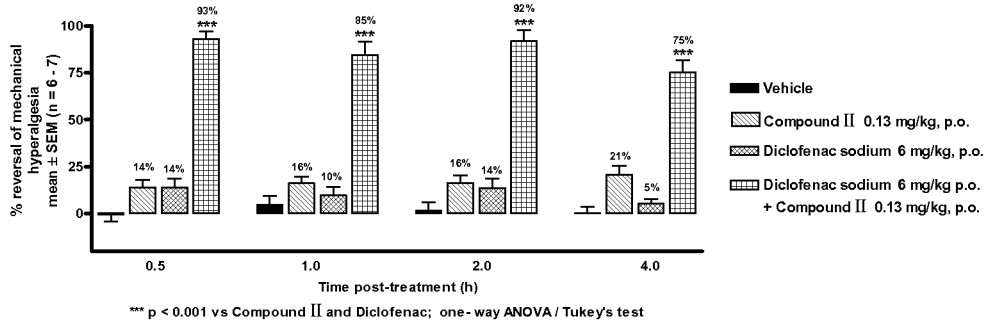
FIG. 13 is a bar graph that represents effect of Compound II (0.13 mg/kg), diclofenac sodium (6 mg/kg) and their combination on FCA-induced mechanical hyperalgesia in male SD rats.

Compound II (0.13 mg/kg) and diclofenac sodium (6 mg/kg) produced only moderate effect with a maximal of 21 & 14% reversal of hyperalgesia respectively. Combination of Compound II and diclofenac sodium produced significantly superior efficacy (synergistic effect) compared to the sum of efficacies of individual agents as shown in FIG. 13. The combination has produced a maximum of 93% reversal of hyperalgesia.

Example 10

The Effect of Compound II Disodium Salt and Naproxen, and their Combination in FCA-Induced Inflammatory Mechanical Hyperalgesia in Male SD Rats Naïve withdrawal thresholds of the left hind paw to an increasing pressure (g) stimulus were measured in rats using the analgesymeter. Freund's Complete Adjuvant (FCA) was injected (30 μl) into the plantar region of left paw of rats to induce the inflammatory hyperalgesia. Mechanical hyperalgesia (24 h after FCA injection) was assessed both pre- & post-dosing of drugs by measuring hind paw withdrawal thresholds. Rats were orally dosed with vehicle, Naproxen, Compound II disodium salt and combination (Naproxen+Compound II—simultaneously). The effect of Compound II, Naproxen and their combination, in FCA-induced inflammatory mechanical hyperalgesia in male SD rats, was evaluated using Randall-Sellitto paw pressure analgesymeter (37215, Ugo Basile, Comerio, Italy) fitted with a wedge-shaped probe. The post-dose paw withdrawal thresholds were measured at 0.5, 1, 2 & 4 h after oral administration. The % reversal of mechanical hyperalgesia was calculated. Animals were weighed and grouped as described in Table 13.

TABLE 13

| Group | Treatment | Dose (mg/kg) Naproxen | Dose (mg/kg) Compound II | Route | No. of animals (N) |
|---|---|---|---|---|---|
| 1 | Vehicle | — | — | p.o. | 8 |
| 2 | Naproxen | 3 | — | p.o. | 8 |
| 3 | Compound II | — | 0.13 | p.o. | 8 |
| 4 | Combination | 3 | 0.13 | p.o. | 8 |

Figure 14:
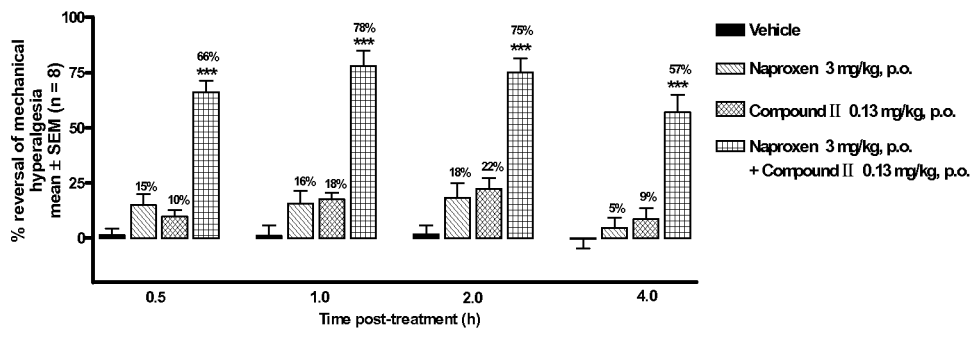
FIG. 14 is a bar graph that represents effect of Compound II (0.13 mg/kg), naproxen (3 mg/kg) and their combination on FCA-induced mechanical hyperalgesia in male SD rats.

Compound II (0.13 mg/kg) and naproxen (3 mg/kg) produced only moderate effect with a maximal of 22 & 18% reversal of hyperalgesia respectively. Combination of Compound II and naproxen produced significantly superior efficacy (synergistic effect) compared to the sum of efficacies of individual agents as shown in FIG. 14. The combination has produced a maximum of 78% reversal of hyperalgesia.

Example 11

The Effect of Compound II Disodium Salt and Meloxicam, and their Combination in FCA-Induced Inflammatory Mechanical Hyperalgesia in Male SD Rats Naïve withdrawal thresholds of the left hind paw to an increasing pressure (g) stimulus were measured in rats using the analgesymeter. Freund's Complete Adjuvant (FCA) was injected (30 μl) into the plantar region of left paw of rats to induce the inflammatory hyperalgesia. Mechanical hyperalgesia (24 h after FCA injection) was assessed both pre- & post-dosing of drugs by measuring hind paw withdrawal thresholds. Rats were orally dosed with vehicle, Meloxicam, Compound II disodium salt and combination (Meloxicam+Compound II—simultaneously). The effect of Compound II, Meloxicam and their combination, in FCA-induced inflammatory mechanical hyperalgesia in male SD rats, was evaluated using Randall-Sellitto paw pressure analgesymeter (37215, Ugo Basile, Comerio, Italy) fitted with a wedge-shaped probe. The post-dose paw withdrawal thresholds were measured at 0.5, 1, 2 & 4 h after oral administration. The % reversal of mechanical hyperalgesia was calculated. Animals were weighed and grouped as described in Table 14.

TABLE 14

| Group | Treatment | Dose (mg/kg) Meloxicam | Dose (mg/kg) Compound II | Route | No. of animals (N) |
|---|---|---|---|---|---|
| 1 | Vehicle | — | — | p.o. | 7 |
| 2 | Meloxicam | 0.5 | — | p.o. | 7 |
| 3 | Compound II | — | 0.13 | p.o. | 7 |
| 4 | Combination | 0.5 | 0.13 | p.o. | 7 |

Figure 15:
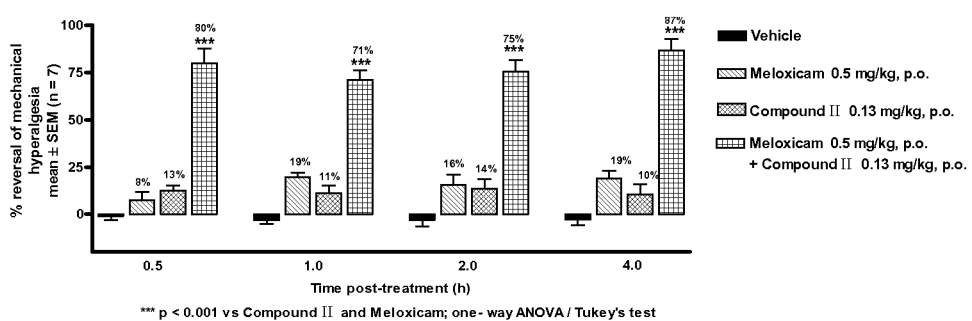
FIG. 15 is a bar graph that represents effect of Compound II (0.13 mg/kg), meloxicam (0.5 mg/kg) and their combination on FCA-induced mechanical hyperalgesia in male SD rats.

Compound II (0.13 mg/kg) and meloxicam (0.5 mg/kg) produced only moderate effect with a maximal of 14 & 19% reversal of hyperalgesia respectively. Combination of Compound II and meloxicam produced significantly superior efficacy (synergistic effect) compared to sum of efficacies of individual agents as shown in FIG. 15. The combination has produced a maximum of 87% reversal of hyperalgesia.

Example 12

The Effect of Compound II Disodium Salt and Paracetamol, and their Combination in FCA-Induced Inflammatory Mechanical Hyperalgesia in Male SD Rats Naïve withdrawal thresholds of the left hind paw to an increasing pressure (g) stimulus were measured in rats using the analgesymeter. Freund's Complete Adjuvant (FCA) was injected (30 μl) into the plantar region of left paw of rats to induce the inflammatory hyperalgesia. Mechanical hyperalgesia (24 h after FCA injection) was assessed both pre- & post-dosing of drugs by measuring hind paw withdrawal thresholds. Rats were orally dosed with vehicle, Paracetamol, Compound II disodium salt and combination (Paracetamol+Compound II—simultaneously). The effect of Compound II, Paracetamol and their combination, in FCA-induced inflammatory mechanical hyperalgesia in male SD rats, was evaluated using Randall-Sellitto paw pressure analgesymeter (37215, Ugo Basile, Comerio, Italy) fitted with a wedge-shaped probe. The post-dose paw withdrawal thresholds were measured at 0.5, 1, 2 & 4 h after oral administration. The % reversal of mechanical hyperalgesia was calculated. Animals were weighed and grouped as described in Table 15.

TABLE 15

| | | Dose (mg/kg) | | | No. of animals (N) |
|---|---|---|---|---|---|
| Group | Treatment | Paracetamol | Compound II | Route | |
| 1 | Vehicle | — | — | p.o. | 8 |
| 2 | Paracetamol | 60 | — | p.o. | 8 |
| 3 | Compound II | — | 0.13 | p.o. | 8 |
| 4 | Combination | 60 | 0.13 | p.o. | 8 |

Figure 16:
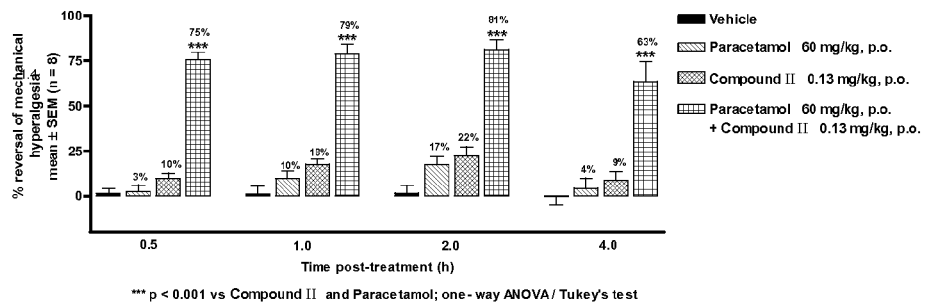
FIG. 16 is a bar graph that represents effect of Compound II (0.13 mg/kg), paracetamol (60 mg/kg) and their combination on FCA-induced mechanical hyperalgesia in male SD rats.

Compound II (0.13 mg/kg) and paracetamol (60 mg/kg) produced only moderate effect with a maximal of 22 & 17% reversal of hyperalgesia respectively. Combination of Compound II and paracetamol produced significantly superior efficacy (synergistic effect) compared to the sum of efficacies of individual agents as shown in FIG. 16. The combination has produced a maximum of 81% reversal of hyperalgesia.

Example 13

To Study the Combinational Effect of Compound II and Duloxetine at Different Doses in Streptozotocin-Induced Diabetic Peripheral Neuropathic Hyperalgesia in Male Sprague-Dawley (SD) Rats Streptozotocin (STZ)-induced neuropathic hyperalgesia in rats is a model to screen potential therapeutics for diabetic painful neuropathy in human patients. Streptozotocin was dissolved in freshly prepared cold citrate buffer (0.1 M, pH —4.4). Diabetes was induced in overnight fasted male Sprague Dawley rats by a single intraperitoneal injection of Streptozotocin (Sigma, 55 mg/kg, i.p). Blood glucose was assayed 1 week post STZ injection using blood glucose meter (Contor TS, Bayer Health Care, India) and animals exhibiting >260 mg/dl blood glucose were considered diabetic. On the day of the experiment ($13^{th}$ day after STZ injection) rats were assessed for mechanical hyperalgesia using Randall-Sellito paw pressure analgesymeter.

Mechanical hyperalgesia was assessed both pre- & post-dosing of drugs by measuring hind paw withdrawal thresholds. Rats were orally dosed with vehicle, different doses of duloxetine hydrochloride, Compound II disodium salt and combinations (duloxetine+Compound II—simultaneously). The post-dose paw withdrawal thresholds were measured at 1, 2 & 4 h after oral administration. The % reversal of mechanical hyperalgesia was calculated as per standard procedure. Animals were weighed and grouped as described in Table 16.

TABLE 16

| | | Dose (mg/kg) | | | No. of animals (N) |
|---|---|---|---|---|---|
| Group | Treatment | Duloxetine HCl | Compound II | Route | |
| 1 | Vehicle | — | — | p.o. | 7 |
| 2 | Duloxetine HCl | 3 | — | p.o. | 7 |

TABLE 16-continued

| | | Dose (mg/kg) | | | No. of animals (N) |
|---|---|---|---|---|---|
| Group | Treatment | Duloxetine HCl | Compound II | Route | |
| 3 | Compound II | — | 0.04 | p.o. | 7 |
| 4 | Combination | 3 | 0.04 | p.o. | 7 |

Figure 17:
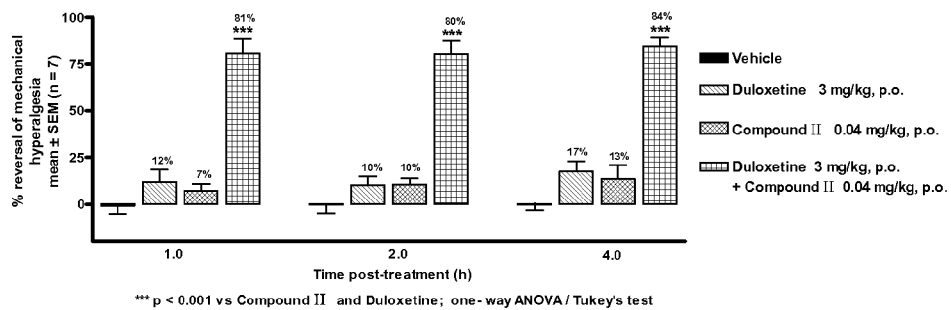
FIG. 17 is a bar graph that represents effect of Compound II (0.04 mg/kg). duloxetine (3 mg/kg) and their combination on streptozocin (STZ)-induced mechanical hyperalgesia in male SD rats.

Compound II (0.04 mg/kg) and duloxetine hydrochloride (3 mg/kg) produced only moderate effect with a maximal of 13 & 17% reversal of hyperalgesia respectively. Combination of Compound II and duloxetine hydrochloride produced significantly superior efficacy (synergistic effect) compared to the sum of efficacies of individual agents as shown in FIG. 17. The combination has produced a maximum of 84% reversal of hyperalgesia.

Example 14

To Study the Combinational Effect of Compound II and Thiocolchicoside in a Freund's Complete Adjuvant (FCA) Model of Inflammatory Pain in Healthy Male Sprague-Dawley (SD) Rats Naïve withdrawal thresholds of the left hind paw to an increasing pressure (g) stimulus were measured in rats using the analgesymeter. Freund's Complete Adjuvant (FCA) was injected (30 µl) into the plantar region of left paw of rats to induce the inflammatory hyperalgesia. Mechanical hyperalgesia (24 h after FCA injection) was assessed both pre- & post-dosing of drugs by measuring hind paw withdrawal thresholds. Rats were orally dosed with vehicle, thiocolchicoside, Compound II disodium salt and combination (thiocolchicoside+Compound II—simultaneously). The effect of Compound II, thiocolchicoside and their combination, in FCA-induced inflammatory mechanical hyperalgesia in male SD rats, was evaluated using Randall-Sellitto paw pressure analgesymeter (37215, Ugo Basile, Comerio, Italy) fitted with a wedge-shaped probe. The post-dose paw withdrawal thresholds were measured at 0.5, 1, 2 & 4 h after oral administration. The % reversal of mechanical hyperalgesia was calculated as per standard procedure. Animals were weighed and grouped as described in Table 17.

TABLE 17

| | | Dose (mg/kg) | | | No. of animals (N) |
|---|---|---|---|---|---|
| Group | Treatment | Thiocolchicoside | Compound II | Route | |
| 1 | Vehicle | — | — | p.o. | 7 |
| 2 | Thiocolchicoside | 0.01 | — | p.o. | 7 |
| 3 | Compound II | — | 0.13 | p.o. | 7 |
| 4 | Combination | 0.01 | 0.13 | p.o. | 7 |

Figure 18:
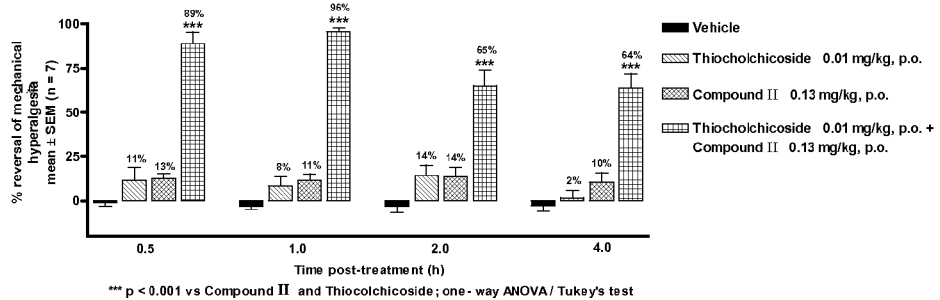
FIG. 18 is a bar graph that represents effect of Compound II (0.13 mg/kg), thiocolchicoside (0.01 mg/kg) and their combination on FCA-induced mechanical hyperalgesia in male SD rats.

Compound II (0.13 mg/kg) and Thiocolchicoside (0.01 mg/kg) produced only moderate effect with a maximal of 14 & 14% reversal of hyperalgesia respectively. Combination of Compound II and thiocolchicoside produced significantly superior efficacy (synergistic effect compared to the sum of efficacies of individual agents as shown in FIG. 18. The combination has produced a maximum of 96% reversal of hyperalgesia.

Figure 19:
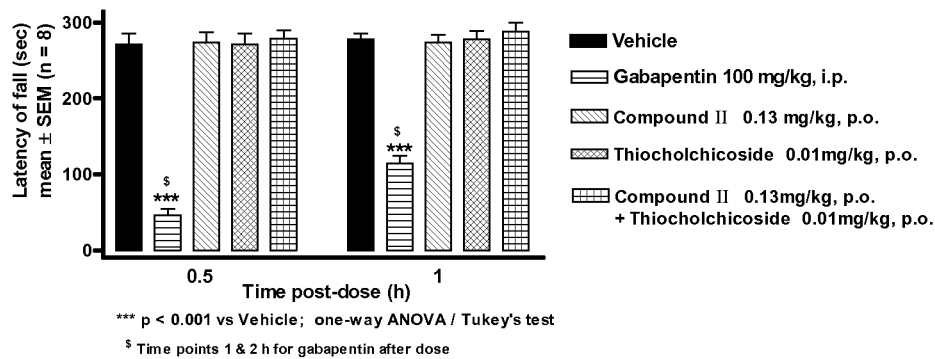
FIG. 19 is a bar graph that represents effect of combination of thiocolchicoside (0.01 mg/kg) and Compound II (0.13 mg/kg) and their combination on motor coordination in rotarod test in male SD rats.

In addition, the chosen doses of Compound II, thiocolchicoside and their combination (n=8) also did not produce any motor deficits as shown in FIG. 19.

Example 15

To Study the Combinational Effect of Compound II and Pregabalin in Spinal Nerve Ligation (SNL) Injury-Induced Neuropathic Hyperalgesia in Male Sprague-Dawley (SD) Rats Spinal nerve ligation (SNL) injury in rats induces neuropathic mechanical hyperalgesia in this Chung's model. Rats were anesthetized using ketamine/xylazine (40/5 mg/kg, i.p.) and a 2-3 cm longitudinal incision was made in the lumbar spinal region, 5-6 mm lateral to the midline and above the lower lumbar vertebrae and the rostral sacrum, exposing the paraspinal muscles on the left side. The paraspinal muscles were isolated using blunt-tipped scissors for exposing L6 transverse process. The L6 transverse process was cut with the help of blunt-tipped scissor to visualize the left L5 spinal nerves. The nerves were cleaned from adhering tissue and were tightly ligated using 7.0 silk sutures (EP 1.5, Pearsalls Ltd) (Somerset, UK). The wound was closed with muscle & skin sutures and Povidone-iodine solution was applied every day till complete healing. Parenteral antibiotic (CILANEM—a combination of Imipenem and Cilastatin, @ 10 mg/kg/day, i.p) treatment was also provided to the operated animals for the first 3 days after surgery. Animals were allowed to recover in their home cage for 7 days (Kim and Chung, 1992). Mechanical hyperalgesia was assessed by measuring hind paw withdrawal to an increasing pressure (g) stimulus, using an analgesymeter (Ugo Basile, Italy) fitted with a wedge-shaped probe.

Mechanical hyperalgesia was assessed both pre- & post-dosing of drugs by measuring hind paw withdrawal thresholds. Rats were orally dosed with vehicle, pregabalin, Compound II disodium salt and combination (pregabalin+Compound II—simultaneously). The post-dose paw withdrawal thresholds were measured at 0.5, 1, 2 & 4 h after oral administration. The % reversal of mechanical hyperalgesia was calculated as per standard procedure. Animals were weighed and grouped as described in Table 18.

TABLE 18

| Group | Treatment | Dose (mg/kg) Pregabalin | Dose (mg/kg) Compound II | Route | No. of animals (N) |
|---|---|---|---|---|---|
| 1 | Vehicle | — | — | p.o. | 8 |
| 2 | Pregabalin | 1 | — | p.o. | 8 |
| 3 | Compound II | — | 0.13 | p.o. | 8 |
| 4 | Combination | 1 | 0.13 | p.o. | 8 |

Figure 20:
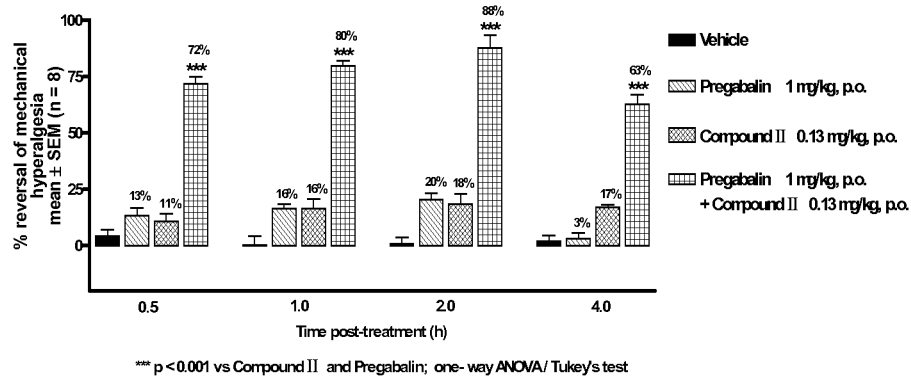
FIG. 20 is a bar graph that represents effect of Compound II (0.13 mg/kg), Pregabalin (1 mg/kg) and their combination on Spinal nerve ligation (SNL)-induced mechanical hyperalgesia in male SD rats.

Compound II (0.13 mg/kg) and pregabalin (1 mg/kg) produced only moderate effect with a maximal of 18 & 20% reversal of hyperalgesia respectively. Combination of Compound II and pregabalin produced significantly superior efficacy (synergistic effect) compared to the sum of efficacies of individual agents as shown in FIG. 20. The combination has produced a maximum of 88% reversal of hyperalgesia.

Example 16

To Study the Combinational Effect of Compound III and Diclofenac Sodium in a Freund's Complete Adjuvant (FCA) Model of Inflammatory Pain in Healthy Male Sprague-Dawley (SD) Rats Naïve withdrawal thresholds of the left hind paw to an increasing pressure (g) stimulus were measured in rats using the analgesymeter. Freund's Complete Adjuvant (FCA) was injected (30 µl/100 µl) into the plantar region of left paw of rats to induce the mechanical/thermal hyperalgesia, respectively. Mechanical/Thermal hyperalgesia (24 h after FCA injection) was assessed both pre- & post-dosing of drugs by measuring hind paw withdrawal thresholds. Rats were orally dosed with vehicle, Diclofenac sodium, Compound III disodium salt and combination (Diclofenac sodium+Compound III—simultaneously). The effect of Compound III, Diclofenac sodium and their combination, in FCA-induced inflammatory mechanical hyperalgesia in male SD rats, was evaluated using either Randall-Sellitto paw pressure analgesymeter (37215, Ugo Basile, Comerio, Italy) fitted with a wedge-shaped probe or Hargreaves apparatus (Ugo Basile) fitted with an infrared stimulus source. The post-dose paw withdrawal thresholds were measured at 0.5, 1, 2 & 4 h after oral administration. The % reversal of mechanical/thermal hyperalgesia was calculated. Animals were weighed and grouped as described in Table 19.

TABLE 19

| Group | Treatment | Dose (mg/kg) Diclofenac sodium | Dose (mg/kg) Compound III | Route | No. of animals (N) |
|---|---|---|---|---|---|
| 1 | Vehicle | — | — | p.o. | 7 |
| 2 | Diclofenac sodium | 6 | — | p.o. | 7 |
| 3 | Compound III | — | 0.039 | p.o. | 7 |
| 4 | Combination | 6 | 0.039 | p.o. | 7 |

Figure 21:
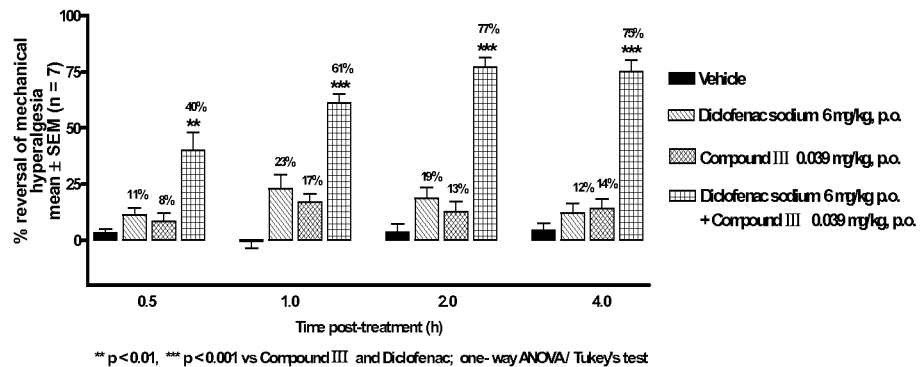
FIG. 21 is a bar graph that represents effect of Compound III (0.039 mg/kg), diclofenac sodium (6 mg/kg) and their combination on FCA-induced mechanical hyperalgesia in male SD rats.

Compound III (0.039 mg/kg) and diclofenac sodium (6 mg/kg) produced only moderate effect with a maximal of 17 & 23% reversal of mechanical hyperalgesia respectively. Combination of Compound III and diclofenac sodium produced significantly superior efficacy (synergistic effect) compared to the sum of efficacies of individual agents as shown in FIG. 21. The combination has produced a maximum of 77% reversal of mechanical hyperalgesia.

Figure 22:
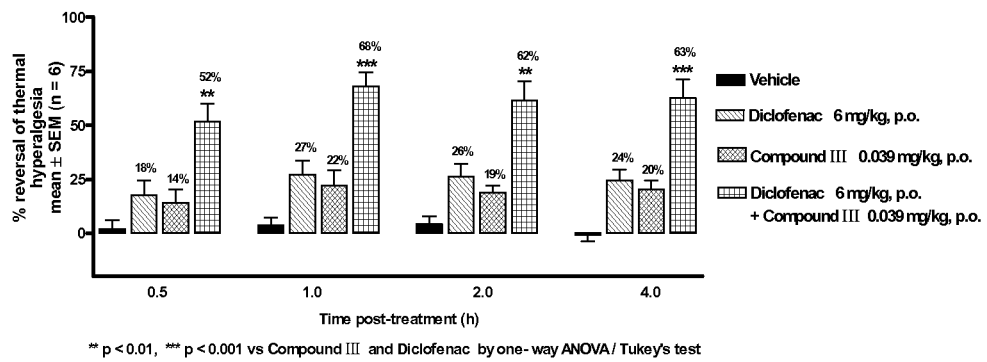
FIG. 22 is a bar graph that represents effect of Compound III (0.039 mg/kg), diclofenac sodium (6 mg/kg) and their combination on FCA-induced thermal hyperalgesia in male SD rats.

Compound III (0.039 mg/kg) and diclofenac sodium (6 mg/kg) produced only moderate effect with a maximal of 22 & 27% reversal of thermal hyperalgesia respectively. Combination of Compound III and diclofenac sodium produced significantly superior efficacy (synergistic effect) compared to the sum of efficacies of individual agents as shown in FIG. 22. The combination has produced a maximum of 68% reversal of thermal hyperalgesia.

Example 17

Effect of Compound III Disodium Salt and Naproxen, and their Combination in FCA-Induced Inflammatory Mechanical Hyperalgesia in Male SD Rats Naïve withdrawal thresholds of the left hind paw to an increasing pressure (g) stimulus were measured in rats using the analgesymeter. Freund's Complete Adjuvant (FCA) was injected (30 μl/100 μl) into the plantar region of left paw of rats to induce the mechanical hyperalgesia, respectively. Mechanical hyperalgesia (24 h after FCA injection) was assessed both pre- & post-dosing of drugs by measuring hind paw withdrawal thresholds. Rats were orally dosed with vehicle, Naproxen, Compound III disodium salt and combination (Naproxen+Compound III—simultaneously). The effect of Compound III, Naproxen and their combination, in FCA-induced inflammatory mechanical hyperalgesia in male SD rats, was evaluated using either Randall-Sellitto paw pressure analgesymeter (37215, Ugo Basile, Comerio, Italy) fitted with a wedge-shaped probe or Hargreaves apparatus (Ugo Basile) fitted with an infrared stimulus source. The post-dose paw withdrawal thresholds were measured at 0.5, 1, 2 & 4 h after oral administration. The % reversal of mechanical hyperalgesia was calculated. Animals were weighed and grouped as described in Table 20.

TABLE 20

| Group | Treatment | Dose (mg/kg) Naproxen | Compound III | Route | No. of animals (N) |
|---|---|---|---|---|---|
| 1 | Vehicle | — | — | p.o. | 7 |
| 2 | Naproxen | 3 | — | p.o. | 7 |
| 3 | Compound III | — | 0.039 | p.o. | 7 |
| 4 | Combination | 3 | 0.039 | p.o. | 7 |

Figure 23:
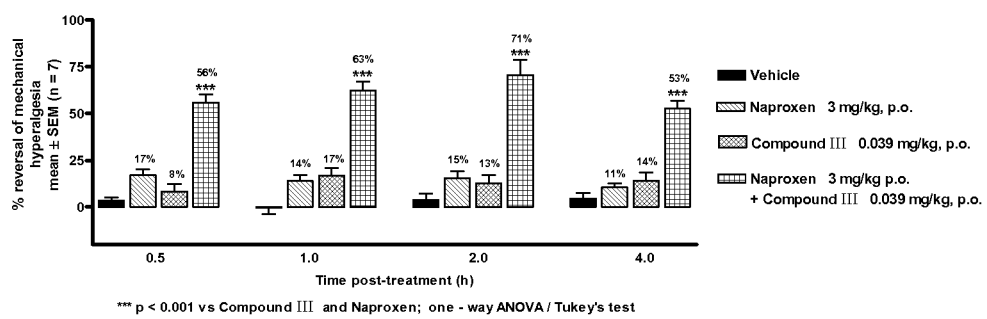
FIG. 23 is a bar graph that represents effect of Compound III (0.039 mg/kg), naproxen (3 mg/kg) and their combination on FCA-induced mechanical hyperalgesia in male SD rats.

Compound III (0.039 mg/kg) and naproxen (3 mg/kg) produced only moderate effect with a maximal of 17 & 17% reversal of mechanical hyperalgesia respectively. Combination of Compound III and naproxen produced significantly superior efficacy (synergistic effect) compared to the sum of efficacies of individual agents as shown in FIG. 23. The combination has produced a maximum of 71% reversal of mechanical hyperalgesia.

Example 18

To Study the Combinational Effect of Compound III and Duloxetine in Streptozotocin-Induced Diabetic Peripheral Neuropathic Hyperalgesia in Male Sprague-Dawley (SD) Rats Streptozotocin (STZ)-induced neuropathic hyperalgesia in rats is a model to screen potential therapeutics for diabetic painful neuropathy in human patients. Streptozotocin was dissolved in freshly prepared cold citrate buffer (0.1 M, pH —4.4). Diabetes was induced in overnight fasted male Sprague Dawley rats by a single intraperitoneal injection of Streptozotocin (Sigma, 55 mg/kg, i.p). Blood glucose was assayed 1 week post STZ injection using blood glucose meter (Contor TS, Bayer Health Care, India) and animals exhibiting >260 mg/dl blood glucose were considered diabetic. On the day of the experiment ($13^{th}$ day after STZ injection) rats were assessed for mechanical hyperalgesia using Randall-Sellito paw pressure analgesymeter.

Mechanical hyperalgesia was assessed both pre- & post-dosing of drugs by measuring hind paw withdrawal thresholds. Rats were orally dosed with vehicle, different doses of duloxetine hydrochloride, Compound III disodium salt and combinations (duloxetine+Compound III—simultaneously). The post-dose paw withdrawal thresholds were measured at 0.5, 1, 2 & 4 h after oral administration. The % reversal of mechanical hyperalgesia was calculated as per standard procedure. Animals were weighed and grouped as described in Table 21.

TABLE 21

| Group | Treatment | Dose (mg/kg) Duloxetine HCl | Compound III | Route | No. of animals (N) |
|---|---|---|---|---|---|
| 1 | Vehicle | — | — | p.o. | 7 |
| 2 | Duloxetine HCl | 3 | — | p.o. | 7 |
| 3 | Compound III | — | 0.04 | p.o. | 7 |
| 4 | Combination | 3 | 0.04 | p.o. | 7 |

Figure 24:
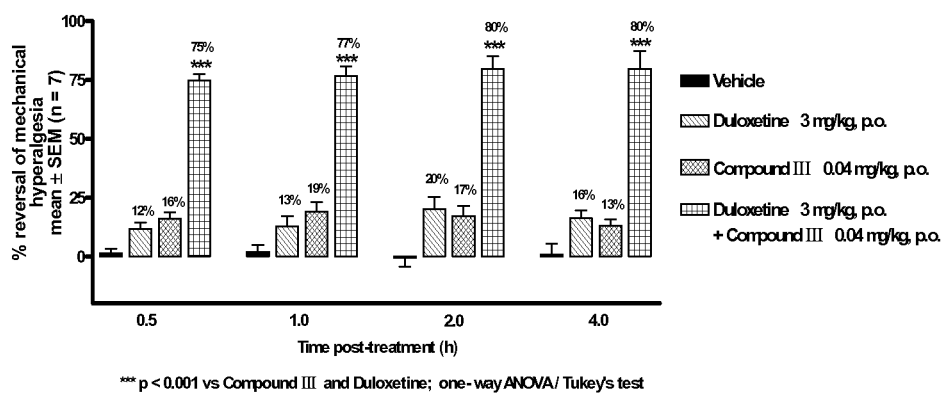
FIG. 24 is a bar graph that represents effect of Compound III (0.04 mg/kg), duloxetine (3 mg/kg) and their combination on STZ-induced mechanical hyperalgesia in male SD rats.

Compound III (0.04 mg/kg) and duloxetine hydrochloride (3 mg/kg) produced only moderate effect with a maximal of 19 & 20% reversal of hyperalgesia respectively. Combination of Compound III and duloxetine hydrochloride produced significantly superior efficacy (synergistic effect) compared to the sum of efficacies of individual agents as shown in FIG. 24. The combination has produced a maximum of 80% reversal of hyperalgesia.

Example 19

To Study the Combinational Effect of Compound III and Naproxen in a Monosodium Iodo Acetate (MIA)-Osteoarthritis Model of Inflammatory Pain in Healthy Male Sprague-Dawley (SD) Rats After recording naïve withdrawal thresholds of the left hind paw to an increasing pressure (g) stimulus were measured in rats using the dynamic von Frey aesthesiometer, rats were briefly anaesthetized with 2% isoflurane and $O_2$ mixture and given intraarticular (i.a.) injection of MIA (5 mg per rat in 50 μl) through the intrapatellar ligament of the left knee (Combe et al., 2004). MIA was dissolved in 0.9% sterile saline and administered using a 26½ gauge needle. Contralateral knees were injected intra-articularly with 50 μl of 0.9% sterile saline. On the day of the experiment (20 h after MIA injection), rats were evaluated for pre-dose mechanical punctate allodynia to assess the effect of MIA. After regrouping the rats after randomization, the pre- & post-dose mechanical allodynia was assessed for both hind paws. Rats were orally dosed with vehicle, naproxen, Compound III disodium salt and combination (Naproxen+Compound III—simultaneously). The effect of Compound III, naproxen and their combination, in MIA-osteoarthritis induced mechanical allodynia in male SD rats, was evaluated using dynamic von Frey aesthesiometer (Ugo Basile) fitted with a filament pressure stimulus (force 0 to 50 g, in 6 sec ramp) and a plexi glass chamber so that the plantar surface of paw can be accessed from beneath a stainless steel mesh. The post-dose paw withdrawal thresholds to mechanical allodynia were measured at 0.5, 1, 2 & 4 h after oral administration. The % reversal of punctate allodynia was calculated as per standard procedure. Animals were weighed and grouped as described in Table 22.

TABLE 22

| Group | Treatment | Dose (mg/kg) Naproxen | Dose (mg/kg) Compound III | Route | No. of animals (N) |
|---|---|---|---|---|---|
| 1 | Vehicle | — | — | p.o. | 8 |
| 2 | Naproxen | 3 | — | p.o. | 8 |
| 3 | Compound III | — | 0.132 | p.o. | 8 |
| 4 | Combination | 3 | 0.132 | p.o. | 8 |

Figure 25:
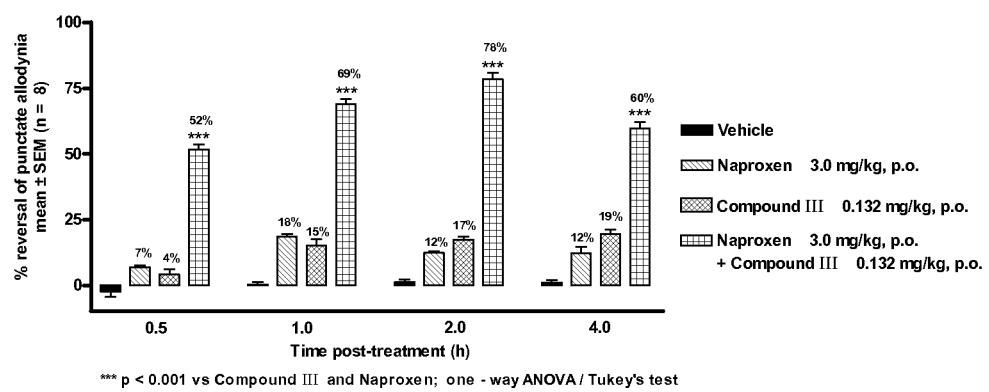
FIG. 25 is a bar graph that represents effect of Compound III (0.132 mg/kg), naproxen (3.0 mg/kg) and their combination on MIA-induced punctate allodynia in male SD rats.

Compound III (0.132 mg/kg) and naproxen (3 mg/kg) produced only moderate effect with a maximal of 19 & 18% reversal of mechanical punctate allodynia respectively. Combination of Compound III and naproxen produced significantly superior efficacy (synergistic effect) compared to the sum of efficacies of individual agents as shown in FIG. 25. The combination has produced a maximum of 78% reversal of mechanical allodynia.

The invention claimed is:

1. A method of treating diabetic neuropathic pain in a subject in need thereof comprising administering to the subject the pharmaceutical composition comprising:
   (i) a transient receptor potential ankyrin-1 ("TRPA1") antagonist compound which is N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide or a pharmaceutically acceptable salt thereof, and
   (ii) an analgesic agent which is duloxetine or a pharmaceutically acceptable salt thereof, wherein the TRPA1 antagonist and the analgesic agent are present in a weight ratio ranging from about 1:1 to about 1:10.

2. The method according to claim 1, wherein the TRPA1 antagonist is N-{4-[2,4-difluoro-3-(trifluormethyl)phenyl]-1,3-thiazol-2-yl}-2-(1,3-dimethyl-2,4-dioxo-1,2,3,4-tetrahydrothieno[2,3-d]pyrimidin-5-yl)acetamide potassium.

3. The method according to claim 1, wherein the neuropathic pain is diabetic peripheral neuropathy (DPN).

4. The pharmaceutical composition according to claim 1, wherein the analgesic agent is duloxetine or pharmaceutically acceptable salts thereof.

5. A method of treating diabetic neuropathic pain in a subject in need thereof comprising administering to the subject the pharmaceutical composition comprising:
   (i) a transient receptor potential ankyrin-1 ("TRPA1") antagonist which is N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide or a pharmaceutically acceptable salt thereof, and
   (ii) an analgesic agent which is pregabalin or a pharmaceutically acceptable salt thereof, wherein the TRPA1 antagonist and the analgesic agent are present in a weight ratio ranging from about 1:1 to about 1:10.

6. The method to claim 1, wherein N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide or pharmaceutically acceptable salt thereof is present in the range from about 5 mg to about 1000 mg.

7. The method according to claim 1, wherein N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-]pyrimidin-5-yl)acetamide or pharmaceutically acceptable salt thereof is present in the range from about 10 mg to about 750 mg.

8. The method according to claim 1, wherein the N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide or pharmaceutically acceptable salt thereof is present in the range from about 50 mg to about 500 mg.

9. The method according to claim 1, wherein N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-]pyrimidin-5-yl)acetamide or pharmaceutically acceptable salt thereof and the analgesic agent are present in fixed dose combination.

10. The method according to claim 1, wherein the pharmaceutical composition is in the form of a tablet, capsule, granules, beads, pellets, solution, suspension, emulsion, powder, or dry syrup.

* * * * *